United States Patent
Dunn et al.

(10) Patent No.: US 12,297,276 B2
(45) Date of Patent: May 13, 2025

(54) ANTI-TEM1 ANTIBODIES AND ANTIGEN-BINDING PORTIONS THEREOF

(71) Applicants: Ludwig Institute for Cancer Research Ltd, Zurich (CH); Centre Hospitalier Universitaire Vaudois, Lausanne (CH); Université de Lausanne, Lausanne (CH)

(72) Inventors: Steven M. Dunn, Epalinges (CH); Julie K. Fierle, Epalinges (CH); George Coukos, Epalinges (CH)

(73) Assignees: Ludwig Institute for Cancer Research Ltd, Zurich (CH); Centre Hospitalier Universitaire Vaudois, Lausanne (CH); Universite de Lausanne, Lausanne (CH)

( * ) Notice: Subject to any disclaimer, the term of this patent is extended or adjusted under 35 U.S.C. 154(b) by 805 days.

(21) Appl. No.: 17/613,823

(22) PCT Filed: May 29, 2020

(86) PCT No.: PCT/US2020/035157
§ 371 (c)(1),
(2) Date: Nov. 23, 2021

(87) PCT Pub. No.: WO2020/243455
PCT Pub. Date: Dec. 3, 2020

(65) Prior Publication Data
US 2022/0227872 A1    Jul. 21, 2022

Related U.S. Application Data

(60) Provisional application No. 62/855,559, filed on May 31, 2019.

(51) Int. Cl.
| | | |
|---|---|---|
| *C07K 16/28* | (2006.01) |
| *A61K 39/00* | (2006.01) |
| *A61P 35/00* | (2006.01) |
| *C07K 14/705* | (2006.01) |
| *C07K 14/725* | (2006.01) |

(52) U.S. Cl.
CPC ...... *C07K 16/2851* (2013.01); *A61K 39/4611* (2023.05); *A61K 39/4631* (2023.05); *A61K 39/4633* (2023.05); *A61K 39/464402* (2023.05); *A61P 35/00* (2018.01); *C07K 14/7051* (2013.01); *C07K 14/70521* (2013.01); *A61K 2039/505* (2013.01); *A61K 2239/38* (2023.05); *A61K 2239/46* (2023.05); *C07K 2317/31* (2013.01); *C07K 2317/33* (2013.01); *C07K 2317/41* (2013.01); *C07K 2317/55* (2013.01); *C07K 2317/622* (2013.01); *C07K 2317/732* (2013.01); *C07K 2317/75* (2013.01); *C07K 2317/92* (2013.01); *C07K 2319/03* (2013.01)

(58) Field of Classification Search
CPC ............ C07K 16/2851; C07K 14/7051; C07K 14/70521; C07K 2317/31; C07K 2317/33; C07K 2317/41; C07K 2317/55; C07K 2317/622; C07K 2317/732; C07K 2317/75; C07K 2317/92; C07K 2319/03; C07K 16/2809; C07K 2317/21; C07K 2317/64; C07K 2317/73; A61K 39/4611; A61K 39/4631; A61K 39/4633; A61K 39/464402; A61K 2039/505; A61K 2239/38; A61K 2239/46; A61K 2239/10; A61K 39/39; A61P 35/00
See application file for complete search history.

(56) References Cited

U.S. PATENT DOCUMENTS

| | | | |
|---|---|---|---|
| 2008/0085241 | A1 | 4/2008 | Stassar et al. |
| 2015/0337051 | A1* | 11/2015 | O'Shannessy .......... A61P 35/00 536/23.53 |
| 2017/0342152 | A1 | 11/2017 | Pearse et al. |
| 2020/0283508 | A1* | 9/2020 | Ko ..................... A61K 47/6835 |

FOREIGN PATENT DOCUMENTS

| | | |
|---|---|---|
| EP | 3202788 A1 | 8/2017 |
| WO | 2011060233 A1 | 5/2011 |
| WO | 2014164544 A1 | 10/2014 |

OTHER PUBLICATIONS

Rudikoff et. al. PNAS 79 p. 1979-1989 (Year: 1982).*
Almagro et. al., Front. Immunol. 2018; 8:1751 (Year: 2018).*
Li et al., "Antibody-based tumor vascular theranostics targeting endosialin/TEM1 in a new mouse 1-3 tumor vascular model", Cancer Biol Ther. 2014, vol. 15(4), p. 443-451.
UniProtKB_A0A1C7DD21, Submitted name: Uncharacterized protein, Accession No. A0A1C7DD21. Last Modified: Nov. 30, 2016. [online]. [Retrieved on Aug. 10, 2020]. Retrieved from the Internet:< URL: https://www.uniprot.org/uniprot/AOA1C7DD21 <http://www.uniprot.org/uniprot/AOA1C7DD21>> Submitted Name; and Sequence (331 a.a.), the region between amino acid residues 221-233, 4 pages.

(Continued)

*Primary Examiner* — Anand U Desai
*Assistant Examiner* — Kathleen Cunningchen
(74) *Attorney, Agent, or Firm* — Fox Rothschild LLP

(57) ABSTRACT

Provided herein are antibodies and antigen-binding portions thereof that bind to tumor endothelial marker 1 (TEM1), as well as methods of using the disclosed antibodies and antigen-binding portions thereof, including methods of treating cancer, reducing tumor growth, reducing tumor metastasis, and/or reducing tumor-associated fibrosis in a subject in need thereof.

32 Claims, 13 Drawing Sheets
Specification includes a Sequence Listing.

(56) References Cited

OTHER PUBLICATIONS

UniProtKB_W6Y0J9, BRCT domain-containing protein. Accession No. W6Y0J9. Last Modified: Apr. 16, 2014. [online]. [Retrieved on Aug. 10, 2020]. Retrieved from the Internet:< URL: https://www.uniprot.org/uniprot/W6YOJ9 <http://www.uniprot.org/uniprot/W6YOJ9>> Recommended Name; and Sequence (391 a.a.), the region between amino acid residues 235-244, 5 pages.

International Search Report and Written Opinion mailed Oct. 26, 2020 for related International Application No. PCT/US20/35157, 14 pages.

Raum Tobias Jet Al: "Novel primate-crossreactive BiTE antibodies that eliminate cancer cells expressing cMet, IGFR-1, FAP-alpha, PSCA, Endosialin, CAIX or Her2/neu", Cancer Res. vol. 70, No. 8S, A2434, 2010.

Extended European Search Report for European Patent Application No. 20814554.0 dated Jun. 28, 2023, 9 pages.

* cited by examiner

Fig. 1A
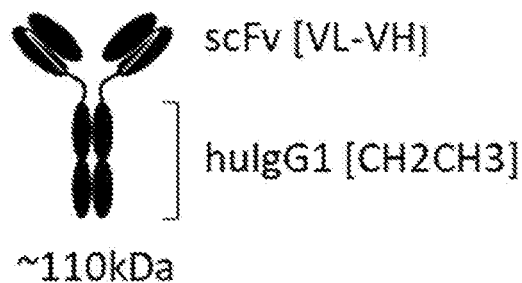
Fig. 1B
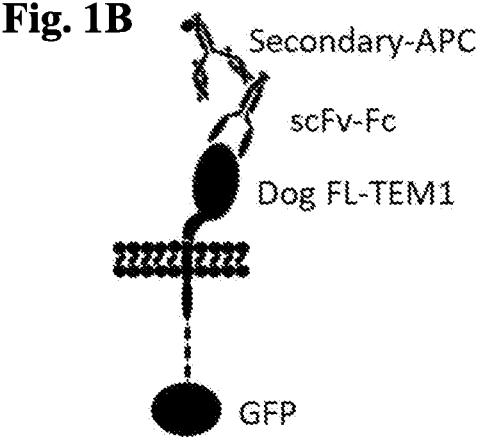
Fig. 1C
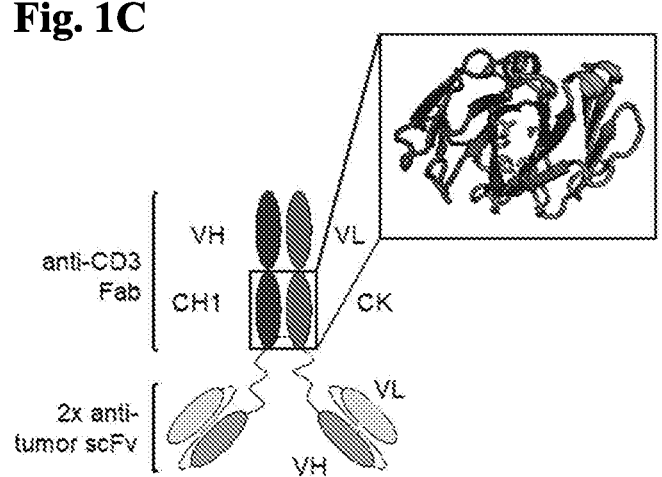
Fig. 1D
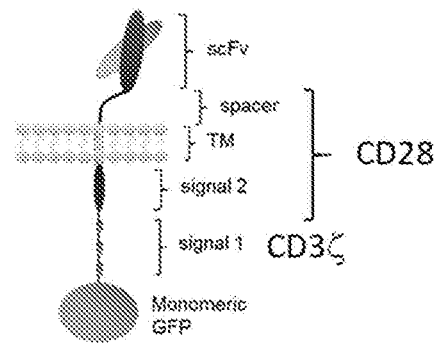
Figure 1

Ligand: hTEM1-SpyC  Ligand: 1C1/1C1mut scFv-Fc
Analyte: 1C1 BiTE  Analyte: hTEM1-FL

1C1_VH_CDR3 [CASL[T]SYYGDPTGFDYW]

1C1mut_VH_CDR3 [CASL[I]SYYGDPTGFDYW]

time (sec)

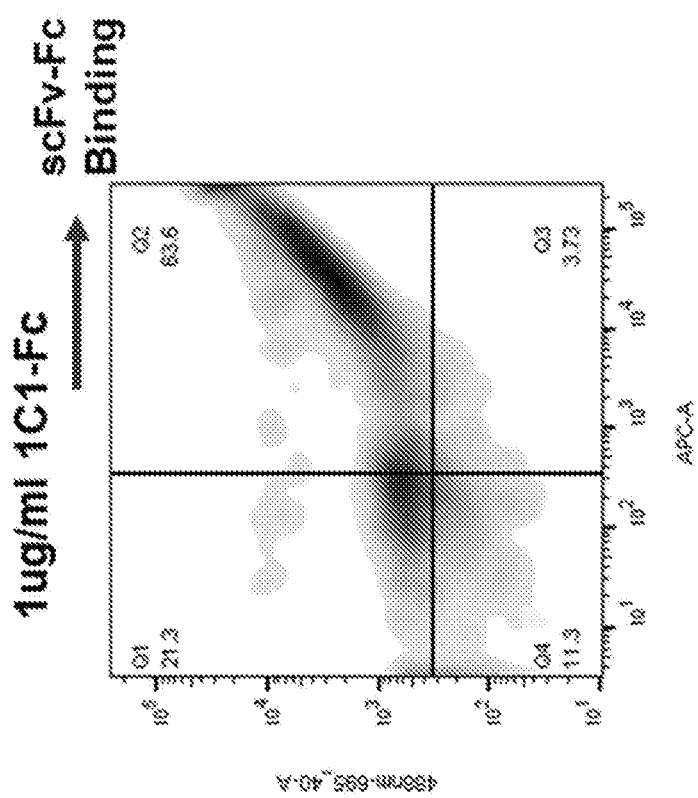
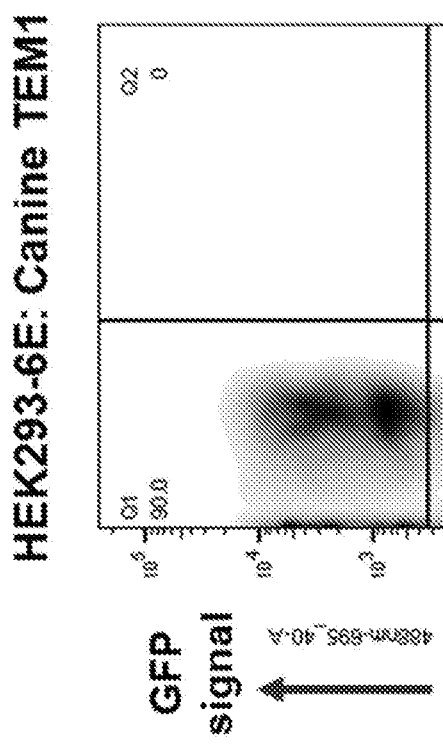
Fig. 6B
Fig. 6A
Figure 6

Fig. 12A
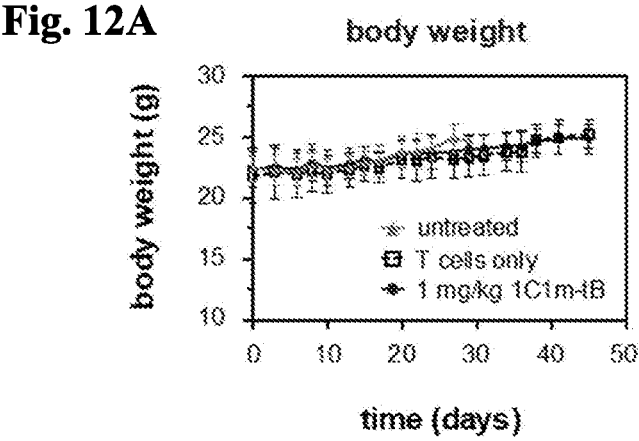
Fig. 12B
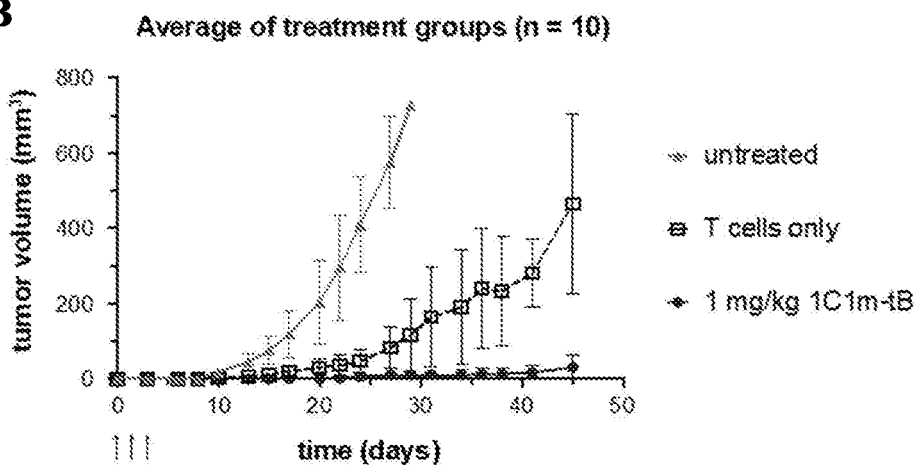
Fig. 12C
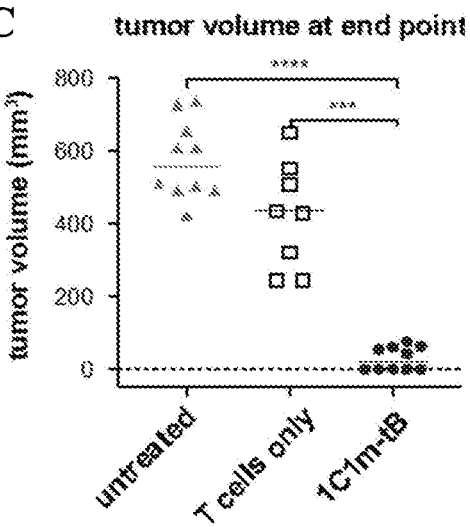
Figure 12

ANTI-TEM1 ANTIBODIES AND ANTIGEN-BINDING PORTIONS THEREOF

FIELD OF THE INVENTION

The present invention relates generally to the field of molecular biology. More particularly, the invention provides antibodies and antigen-binding portions thereof that bind to mammalian tumor endothelial marker 1 (TEM1) and therapeutic compositions thereof, as well as methods of using such antibodies, including methods for treating cancer and methods of diagnosis.

BACKGROUND

The present disclosure relates to the generation of antibodies and antigen-binding portions thereof that recognize and bind tumor endothelial marker 1 (TEM1), a cell surface antigen characteristic of tumor pericytes and cells of tumor stroma.

TEM1, also known as CD248 or endosialin, is a highly restricted 165-kDa cell surface glycoprotein expressed by tumor pericytes and fibroblasts in a broad range of human cancers but not detected in the respective cell types in many normal tissues. TEM1 is a 165-kDa single-pass transmembrane glycoprotein that has been classified as a C type lectin-like membrane receptor. It has multiple extracellular domains consisting of three EGF-like domains, a sushi-like domain, and a C lectin-like domain. TEM1 was shown to interact with proteins of the extracellular matrix (Fibronectin, Collagen I), mediating cell adhesion and migration. TEM1 also interacts with the tumor secreted protein LGALS3BP, a protein involved in cell adhesion and migration, acting also as a pro-angiogenic factor.

TEM1 is broadly expressed in human cancer, including but not limited to, sarcomas and carcinomas. Due to the protein's expression across the stroma of many human tumors, the low to absent expression of TEM1 in normal tissues, and the accessibility of TEM1 from the vascular circulation, TEM1 is an attractive molecule for diagnostics and therapeutics.

SUMMARY OF THE INVENTION

Provided herein are antibodies and antigen-binding portions thereof that selectively bind to TEM1, as well as methods of using such antibodies and antigen-binding portions thereof.

In one aspect, provided is an antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein HCDR1 comprises the amino acid sequence of SEQ ID NO:16 or SEQ ID NO:19; HCDR2 comprises the amino acid sequence of SEQ ID NO:17 or SEQ ID NO: 20; HCDR3 comprises the amino acid sequence of SEQ ID NO:22 or SEQ ID NO:48; LCDR1 comprises the amino acid sequence of SEQ ID NO:11 or SEQ ID NO: 14; LCDR2 comprises the amino acid sequence SNN or the sequence of SEQ ID NO: 15; and LCDR3 comprises the amino acid sequence of SEQ ID NO:13.

In one aspect, provided is an antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein HCDR1 comprises the amino acid sequence of SEQ ID NO:16 or SEQ ID NO:19; HCDR2 comprises the amino acid sequence of SEQ ID NO:17 or SEQ ID NO: 20; HCDR3 comprises the amino acid sequence of SEQ ID NO:18 or SEQ ID NO: 21; LCDR1 comprises the amino acid sequence of SEQ ID NO:11 or SEQ ID NO: 14; LCDR2 comprises the amino acid sequence SNN or the sequence of SEQ ID NO: 15; and LCDR3 comprises the amino acid sequence of SEQ ID NO:13.

In one aspect, provided is an antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein HCDR1 comprises the amino acid sequence of SEQ ID NO:28 or SEQ ID NO:31; HCDR2 comprises the amino acid sequence of SEQ ID NO:29 or SEQ ID NO: 32; HCDR3 comprises the amino acid sequence of SEQ ID NO:30 or SEQ ID NO: 33; LCDR1 comprises the amino acid sequence of SEQ ID NO:23 or SEQ ID NO:26; LCDR2 comprises the amino acid sequence DAS or the sequence of SEQ ID NO:27; and LCDR3 comprises the amino acid sequence of SEQ ID NO:25.

In one aspect, provided is an antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein HCDR1 comprises the amino acid sequence of SEQ ID NO:39 or SEQ ID NO:42; HCDR2 comprises the amino acid sequence of SEQ ID NO:40 or SEQ ID NO:43; HCDR3 comprises the amino acid sequence of SEQ ID NO:41 or SEQ ID NO:49; LCDR1 comprises the amino acid sequence of SEQ ID NO:34 or SEQ ID NO:37; LCDR2 comprises the amino acid sequence STY or the sequence of SEQ ID NO:38; and LCDR3 comprises the amino acid sequence of SEQ ID NO:36.

In one embodiment, the anti-TEM1 antibody or antigen-binding portion thereof comprises a heavy chain variable region comprising a sequence that is at least 90% identical to SEQ ID NO: 6 and a light chain variable region comprising a sequence that is at least 90% identical to SEQ ID NO: 5. In one embodiment, the anti-TEM1 antibody or antigen-binding portion thereof comprises a heavy chain variable region comprising the sequence of SEQ ID NO: 6 and a light chain variable region comprising the sequence of SEQ ID NO: 5.

In one embodiment, the anti-TEM1 antibody or antigen-binding portion thereof comprises a heavy chain variable region comprising a sequence that is at least 90% identical to SEQ ID NO: 4 and a light chain variable region comprising a sequence that is at least 90% identical to SEQ ID NO: 3. In one embodiment, the anti-TEM1 antibody or antigen-binding portion thereof comprises a heavy chain variable region comprising the sequence of SEQ ID NO: 4 and a light chain variable region comprising the sequence of SEQ ID NO: 3.

In one embodiment, the anti-TEM1 antibody or antigen-binding portion thereof comprises a heavy chain variable region comprising a sequence that is at least 90% identical to SEQ ID NO: 8 and a light chain variable region comprising a sequence that is at least 90% identical to SEQ ID NO: 7. In one embodiment, the anti-TEM1 antibody or antigen-binding portion thereof comprises a heavy chain variable region comprising the sequence of SEQ ID NO: 8 and a light chain variable region comprising the sequence of SEQ ID NO: 6.

In one embodiment, the anti-TEM1 antibody or antigen-binding portion thereof comprises a heavy chain variable region comprising a sequence that is at least 90% identical to SEQ ID NO: 10 and a light chain variable region comprising a sequence that is at least 90% identical to SEQ ID NO: 9. In one embodiment, the anti-TEM1 antibody or antigen-binding portion thereof comprises a heavy chain variable region comprising the sequence of SEQ ID NO: 10 and a light chain variable region comprising the sequence of SEQ ID NO: 9.

Provided is an anti-TEM1 antibody or antigen-binding portion thereof, wherein the antibody is selected from antibodies 1C1mut, 1C1, 2B11, and 3B6. Provided is an anti-TEM1 antibody or antigen-binding portion thereof, wherein the antigen-binding portion is provided as a scFv, Fv, Fab', Fab, F(ab')$_2$, scFv-Fc fusion, BiTE, tri-lobed bidirectional T-cell engager (TriloBiTE), chimeric antigen receptor, or diabody.

Provided herein is an antigen-binding portion of an anti-TEM1 antibody disclosed herein wherein the antigen-binding portion is a scFv. In some embodiments, the scFv is fused to the constant region of a Fab. In some embodiments, the antigen-binding portion is fused to the constant region of a Fab using a linker comprising SEQ ID NO:46 or SEQ ID NO:47. In some embodiments, the Fab comprises a VH-CH1 region or fragment thereof and a VL-CL1 region or fragment thereof, wherein the VH-CH1 region is derived from IgG1, and wherein the VL-CL1 region is derived from a kappa light chain. In some embodiments, the VH-CH1 region is derived from human IgG1 and further comprises a S64E and/or a S66V mutation and the VL-CL1 region is derived from a human kappa light chain and further comprises a S69L and/or a T71S mutation. In some embodiments, the Fab binds to a T-cell antigen.

Provided herein is a chimeric antigen receptor (CAR), wherein the CAR comprises an scFv comprising the antigen-binding portion of an anti-TEM1 antibody disclosed herein and further comprises a transmembrane domain and one or more intracellular domains. In some embodiments, the CAR comprises: a spacer derived from CD28, a transmembrane domain derived from CD28, an intracellular domain derived from CD28, and a domain comprising immunoreceptor tyrosine-based activation motifs (ITAMs) derived from CD3-zeta.

Provided herein is an anti-TEM1 antibody or antigen-binding portion thereof, wherein the antibody or antigen-binding portion thereof is a multispecific or a bispecific antibody or antigen-binding portion thereof. In some embodiments, the anti-TEM1 antibody or antigen-binding portion thereof has the isotype IgG1. In some embodiments, the anti-TEM1 antibody or antigen-binding portion thereof is deglycosylated.

Provided herein is an anti-TEM1 antibody or antigen-binding portion thereof, wherein the antibody or antigen-binding portion is conjugated to a therapeutic moiety, an imaging moiety, and/or an affinity tag.

Provided herein is an anti-TEM1 antibody or antigen-binding portion thereof, wherein the antibody or antigen-binding portion thereof competes for binding to TEM1 with an antibody or antigen-binding portion thereof according to according to any of the preceding claims.

Provided herein is a nucleic acid molecule encoding an anti-TEM1 antibody or antigen-binding portion thereof disclosed herein. Provided herein is a vector comprising a nucleic acid molecule encoding an anti-TEM1 antibody or antigen-binding portion thereof disclosed herein. Also provided is a cell comprising vector comprising a nucleic acid molecule encoding an anti-TEM1 antibody or antigen-binding portion thereof disclosed herein.

Provided herein is a method of treating cancer in a subject in need thereof, the method comprising administering to the subject an effective amount of an anti-TEM1 antibody or antigen-binding portion thereof disclosed herein. In some embodiments, the cancer is sarcoma, carcinoma, melanoma, pancreatic cancer, thyroid cancer, lung cancer, colorectal cancer, squamous cancer, prostate cancer, breast cancer, bladder cancer, or gastric cancer.

Provided herein is a method of reducing tumor growth in a subject in need thereof, the method comprising administering to the subject an effective amount of an anti-TEM1 antibody or antigen-binding portion thereof disclosed herein.

Provided herein is a method of reducing tumor metastasis in a subject in need thereof, the method comprising administering to the subject an effective amount of an anti-TEM1 antibody or antigen-binding portion thereof disclosed herein.

Provided herein is a method of reducing tumor-associated fibrosis in a subject in need thereof, the method comprising administering to the subject an effective amount of an anti-TEM1 antibody or antigen-binding portion thereof disclosed herein.

BRIEF DESCRIPTION OF THE FIGURES

FIG. 1 illustrates the structures of different anti-TEM1 functional formats described in this disclosure. FIG. 1A is a schematic representation of an scFv-Fc fusion molecule. FIG. 1B is a schematic representation of an anti-TEM1 scFv-Fc fusion molecule utilized in a recombinant cell assay. FIG. 1C is a schematic representation of a TriloBiTE molecule. A tumor antigen-specific scFv is fused to both heavy and light chain of a chimeric humanized anti-CD3 Fab. The human CH1-Ck interface serves as the heterodimerization scaffold and has been reinforced by stabilizing mutations, shown in bold stick representation.

FIG. 1D is a schematic representation of a chimeric antigen receptor (CAR).

FIG. 6 illustrates that 1C1 effectively recognizes canine TEM1+ cells. Binding of anti-TEM1 scFv-Fc 1C1 clone (1 µg/ml) to HEK293-6E suspension cells transiently transfected with a native canine full-length FL-TEM1 reporter construct (FIG. 6A) was determined using FACS (FIG. 6B).

FIG. 12 shows that an anti-TEM1 TriloBiTE reduces the growth of TEM1+ tumors in vivo. Purified human pan-T-cells were activated with CD3 and CD28 and combined with A673 tumor cells prior to co-inoculation at a sub-cutaneous site. For an untreated tumor-only control, no T-cells were used ("untreated"). 1, 24 and 48 h after tumor cell inoculation, mice were injected (I.V., tail vein) with either 1 mg/kg of a TriloBiTE comprising anti-TEM1 scFv 1C1mut or with PBS ("T cells only"). FIG. 12A illustrates that injection of the anti-TEM1 TriloBiTE was well tolerated by the mice. FIG. 12B (tumor volume over time) and FIG. 12C (tumor volume at point of sacrifice) illustrate that bulk human T-cells had a general inhibitory effect on A673 tumor engraftment. However, administration of the anti-TEM1 TriloBiTE completely prevented establishment of tumor (no outgrowth observed a considerable period after the last treatment).

DETAILED DESCRIPTION OF THE INVENTION

Figure 2:
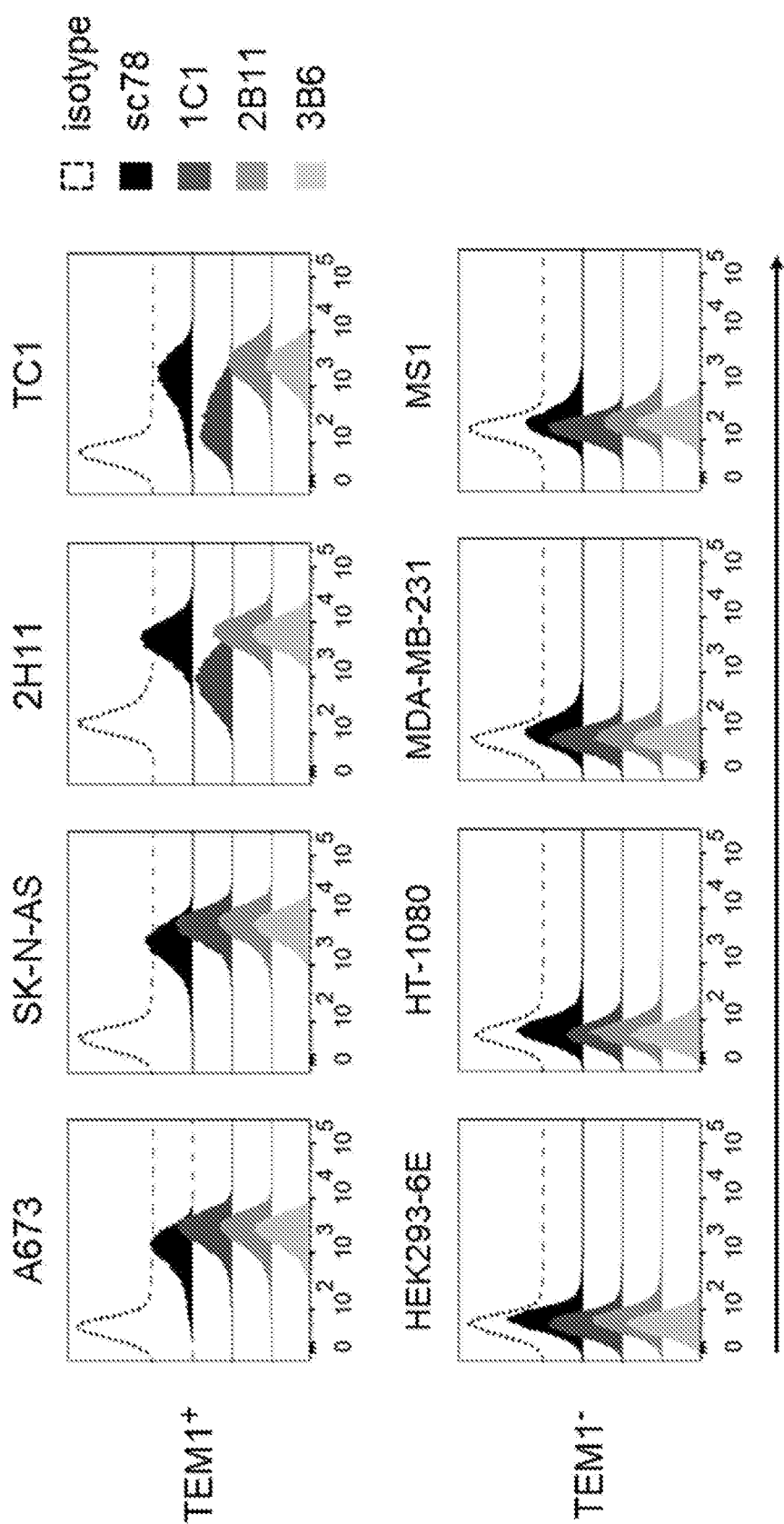
FIG. 2 confirms selective binding of anti-TEM1 scFv-Fcs to human and murine TEM1. 1C1 shows preferential binding to human TEM1$^+$ cells. Binding of reformatted and purified scFv-Fc (hIgG1) clones (2 µg/ml) to human and murine cell lines was determined using fluorescence-activated cell sorting (FACS). A673, human Ewing's sarcoma; SK-N-AS, human neuroblastoma; 2H11, murine tumor vascular endothelium; TC1, murine lung adenocarcinoma; HEK293-6E, human embryonic kidney; HT-1080, human fibrosarcoma; MDA-MB-231, human mammary carcinoma; MS1, murine pancreatic islet endothelium.

Anti-TEM1 Antibodies and Antigen-Binding Portions Thereof.

Provided herein are antibodies and antigen-binding portions thereof that selectively bind to TEM1, as well as methods of using such antibodies and antigen-binding portions thereof. The sequence of human TEM 1 (endosialin precursor; GenPep Accession NP_065137) is provided in SEQ ID NO:1. The sequence of murine TEM1 (UniprotKB/Swiss-Prot: Q91V98 (CD248 MOUSE)) is provided in SEQ ID NO:2. In some embodiments, the anti-TEM1 antibodies or antigen-binding portions thereof disclosed herein bind to human TEM1, to murine TEM1, and/or to canine TEM1.

As used herein, the term "antibody" refers to an immunoglobulin molecule comprising four polypeptide chains, two heavy (H) chains and two light (L) chains inter-connected by disulfide bonds, as well as multimers thereof (e.g., IgM). In a typical antibody, each heavy chain comprises a heavy chain variable region (VH) and a heavy chain constant region. The heavy chain constant region may comprise three domains, CH1, CH2 and CH3. Each light chain may comprise a light chain variable region (VL) and a light chain constant region. The light chain constant region may comprise one domain (CL1). The VH and VL regions can be further subdivided into regions of hypervariability, termed complementarity determining regions (CDRs), interspersed with regions that are more conserved, termed framework regions (FR). Each VH and VL may be composed of three CDRs and four FRs, arranged from amino-terminus to carboxy-terminus in the following order: FR1, CDR1, FR2, CDR2, FR3, CDR3, FR4.

As used herein, the term "Complementarity Determining Regions" (CDRs) refers to portions of an antibody variable domain or antigen-binding portion thereof that are (typically) involved in antigen binding. Each variable domain typically has three CDR regions identified as CDR1, CDR2 and CDR3. Each CDR can comprise amino acid residues from a CDR as defined by e.g. Kabat (i.e., about residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1987, 1991)). Each CDR can also comprise amino acid residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain (Chothia & Lesk 196 J. Mol. Biol. 901 (1987)). In some instances, a CDR can include amino acids from both a CDR region defined according to Kabat and a hypervariable loop. The Kabat residue designations do not always correspond directly with the linear numbering of the amino acid residues (primary amino acid sequence). The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody or antigen-binding portion thereof by alignment of residues of homology in the sequence of the antibody or antigen-binding portion thereof with a "standard" Kabat numbered sequence. Alternatively, a CDR can be defined according to the ImMunoGeneTics (IMGT) system (Lefranc, M. P. et al., Dev. Comp. Immunol., 27, 55-77 (2003)).

As used herein, the terms "antigen-binding portion" of an antibody, and the like, include any naturally occurring, enzymatically obtainable, synthetic, or genetically engineered polypeptide or glycoprotein that specifically binds an antigen to form a complex. Antigen-binding portions of an antibody may be derived, e.g., from full antibody molecules using any suitable standard techniques such as proteolytic digestion or recombinant genetic engineering techniques involving the manipulation and expression of DNA encoding antibody variable and optionally constant domains.

An antigen-binding portion of an antibody may comprise at least one variable domain. In antigen-binding portion having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding portion may contain a monomeric VH or VL domain.

In certain embodiments, an antigen-binding portion may contain at least one variable domain covalently linked to at least one constant domain. Non-limiting, exemplary configurations of variable and constant domains that may be found within an antigen-binding portion disclosed herein include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding portion of an antibody provided herein may comprise a homo-dimer or hetero-dimer (or other multimer) of any of the variable and constant domain configurations listed above in non-covalent association with one another and/or with one or more monomeric VH or VL domain (e.g., by disulfide bond(s)).

In one embodiment, the antigen-binding portion is provided in the form of a Fab fragment comprising or consisting essentially of a variable (VL) and constant (CL) domain of the light chain and a variable domain (VH) and the first constant domain (CH1) of the heavy chain.

In one embodiment, the antigen-binding portion is provided in the form of a Fab' fragment comprising a free sulfhydryl group.

In one embodiment, the antigen-binding portion is provided in the form of F(ab')2 fragment, which comprises a bivalent fragment comprising two Fab' fragments linked by a disulfide bridge at the hinge region.

In one embodiment, the antigen-binding portion is provided in the form of a dAb fragment comprising or consisting essentially of a VH domain.

In one embodiment, the antigen-binding portion is provided in the form of an Fd fragment comprising or consisting essentially of VH and CH1 domains.

In one embodiment, the antigen-binding portion is provided in the form of an Fd' fragment comprising VH and CH1 domains and one or more cysteine residues at the C-terminus of the CH1 domain.

In one embodiment, the antigen-binding portion is provided in the form of a diabody comprising two antigen-binding sites, comprising a heavy chain variable domain (VH) connected to a light chain variable domain (VL) in the same polypeptide chain.

In one embodiment, the antigen-binding portion is provided in the form of an Fv fragment comprising or consisting essentially of the VH and VL domains of antibody, wherein the VH and VL chains of the Fv domains are held together by non-covalent interactions.

In one embodiment, the antigen-binding portion is provided in the form of a single-chain Fv or scFv, which comprises or consists essentially of the VH and VL domains of antibody, such that these domains are present in a single polypeptide chain. In one embodiment, the scFv comprises a polypeptide linker between the VH and VL domains, which allows the scFv to form the desired structure for antigen binding. See, for example, Pluckthun, 113 Pharmacology Monoclonal Antibodies 269 (Rosenburg & Moore, eds., Springer-Verlag, New York, 1994). In some embodiments, the antigen-binding portion comprises a scFv, which is further fused to an Fc domain.

In one embodiment, the antigen-binding portion is provided in the form of a bi-specific T-cell engager (BiTE) comprising two scFv fragments derived from one or two antibodies.

In one embodiment, the antigen-binding portion is provided in the form of a tri-lobed bidirectional T-cell engager (TriloBiTE), wherein the TriloBiTE comprises one or more scFv domains that are linked to the constant region of a Fab. Selectivity and T-cell engagement of the TriloBiTE can be modulated, for example, by varying the antigen target of the Fab, the antigen target(s) of the one or more scFv domains, the number of scFv domains present in the TriloBiTE molecule, the affinity of one or more scFv domains to their respective targets, and the length and composition of the linker fusing the one or more scFvs to the Fab constant region. For example, using a higher-affinity scFv can increase the potency of the T-cell engager. Alternatively, strong antigen binding might also be achieved by using more than one low-affinity or medium-affinity scFv, an approach which can further provide for tumor-selective binding of the T-cell engager to target antigens that are expressed at low levels in normal tissues.

In one embodiment, the one or more scFvs are derived from the same antibody. In one embodiment, the one or more scFvs bind the same antigen, including, but not limited to, TEM1. In one embodiment, the TriloBiTE comprises scFvs that are derived from more than one antibody. In one embodiment, the TriloBiTE comprises scFvs that bind to different antigens. In one embodiment, the TriloBiTE comprises a single anti-TEM1 scFv. In one embodiment, the TriloBiTE comprises two anti-TEM1 scFv.

In one embodiment, the TriloBiTE comprises one high-affinity scFv. In one embodiment, the TriloBiTE comprises two or more low- or medium-affinity scFvs. In one embodiment, the TriloBiTE comprises two low- or medium-affinity scFvs.

In one embodiment, the TriloBiTE comprises a Fab comprising a VH1-CH1 domain and a VL-Cκ domain. In one embodiment, the VH1-CH1 is derived from IgG1. In one embodiment, the VH1-CH1 domain and a VL-Cκ domain are human. In one embodiment, the VH1-CH1 domain comprises an S64E and/or an S66V mutation. In one embodiment, VL-Cκ comprises an S69L and/or a T71S mutation.

In one embodiment, the one or more scFv domains are fused to the C-terminus of the Fab via the constant region of the Fab. In one embodiment, an scFv is fused to the constant region using a linker comprising SEQ ID NOs:46 or 47. In one embodiment, the scFv domain is fused to the VH1-CH1 domain using a linker comprising SEQ ID NO:47. In one embodiment, the scFv domain is fused to the VL-Cκ domain using a linker comprising SEQ ID NO:46.

In one embodiment, the TriloBiTE comprises: (a) a Fab comprising (1) a human VH1-CH1 (IgG1) domain comprising an S64E and an S66V mutation and (2) a human VL-Cx domain comprising an S69L and an T71S mutation and (b) one or two anti-TEM1 scFvs, wherein the one or more scFv domains are fused to the constant region of the Fab using a linker.

In one embodiment, the TriloBiTE comprises: (a) a Fab comprising (1) a human VH1-CH1 (IgG1) domain comprising an S64E and an S66V mutation and (2) a human VL-Cx domain comprising an S69L and an T71S mutation and (b) an anti-TEM1 scFv, which is fused to the VH1-CH1 domain using a linker comprising SEQ ID NO:47 and/or an anti-TEM1 scFv, which is fused to the VL-Cκ domain using a linker comprising SEQ ID NO:46. In some embodiments, the anti-TEM1 scFv comprises any of the CDRs of any of the anti-TEM1 antibodies or antigen-binding portions thereof disclosed herein. In some embodiments, the anti-TEM1 scFv comprises any of the variable heavy and/or variable light chains of any of the anti-TEM1 antibodies or antigen-binding portions thereof disclosed herein. In one embodiment, the Fab is an anti-CD3 Fab.

In one embodiment, the antigen-binding portion is provided in the form of a chimeric antigen receptor (CAR). As used herein, a CAR may refer to artificial T-cell receptor, chimeric T-cell receptor, or chimeric immunoreceptor, for example, and encompass engineered receptors that graft an artificial specificity onto a particular immune effector cell. In some embodiments, CARs direct specificity of the T-cell to a tumor antigen. CARs comprise an intracellular domain, a transmembrane domain, and an extracellular domain comprising a tumor antigen binding region.

In one aspect, provided is a CAR comprising an anti-TEM1 binding portion derived from any of the anti-TEM1 antibodies or antigen-binding portions thereof disclosed herein. In one embodiment, provided is a CAR comprising an anti-TEM1 scFv comprising any of the antigen-binding portions thereof disclosed herein.

In one aspect, the anti-TEM1 binding portion is fused to a transmembrane domain. Non-limiting examples of transmembrane domains suitable for use in the CAR constructs disclosed herein include transmembrane domains derived from CD3ζ, CD28, CD4, CD8, and ICOS. In some embodiments, the anti-TEM1 binding portion is fused to the transmembrane domain using a spacer. Non-limiting examples of spacers suitable for use in the CAR constructs disclosed herein include spacers derived from CD28, CD4, and CD8α, as well as hinge and constant domains derived from IgG or IgD.

In one aspect, the transmembrane domain of the CAR is fused to one or more intracellular domains, wherein at least one of the one or more intracellular domains mediates signal transduction upon antigen binding. Non-limiting examples of intracellular domains to be used in the CARs disclosed herein include intracellular domains derived from CD3ζ, FcR, CD27, CD28, CD137, DAP10, 4-1BB, OX40 and domains comprising immunoreceptor tyrosine-based activation motifs (ITAMs).

In one embodiment, provided is an anti-TEM1 CAR comprising: (1) an anti-TEM1 scFV; (2) a spacer derived from CD28, (3) a transmembrane domain derived from CD28, (4) an intracellular domain derived from CD28, and (4) a domain comprising ITAMs derived from CD3ζ. In some embodiments, the anti-TEM1 CAR comprises any of the CDRs of any of the anti-TEM1 antibodies or antigen-binding portions thereof disclosed herein. In some embodiments, the anti-TEM1 CAR comprises any of the variable heavy and/or variable light chains of any of the anti-TEM1 antibodies or antigen-binding portions thereof disclosed herein.

In some cases, molecules can be co-expressed with the CAR, including costimulatory molecules, reporter genes for imaging (e.g., for positron emission tomography), gene products that conditionally ablate the T-cells upon addition of a pro-drug, homing receptors, chemokines, chemokine receptors, cytokines, and cytokine receptors.

In some embodiment, the anti-TEM1 antibodies and antigen-binding portions thereof disclosed herein are provided in a bispecific or multi-specific format.

In some embodiments, the anti-TEM1 antibody or antigen-binding portion thereof further comprises one or more an antigen-binding portions directed at second tumor antigen. The term "tumor antigen" as used herein includes both tumor associated antigens (TAAs) and tumor specific antigens (TSAs). A tumor associated antigen means an antigen that is expressed on the surface of a tumor cell in higher amounts than is observed on normal cells or an antigen that is expressed on normal cells during fetal development. A tumor specific antigen is an antigen that is unique to tumor cells and is not expressed on normal cells. The term tumor antigen includes TAAs or TSAs that have been already identified and those that have yet to be identified and includes fragments, epitopes and any and all modifications to the tumor antigens. Not-limiting examples of tumor antigens include CD19, CD20, CD30, CD33, CD38, CD133, BCMA, TEM8, EpCAM, ROR1, Folate Receptor, CD70, MAGE-1, MAGE-2, MAGE-3, CEA, tyrosinase, midkin, BAGE, CASP-8, β-catenin, CA-125, CDK-1, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR GOLGA, BMI1, COX-2, EGFRvIII, EZH2, LICAM, Livin, Livinβ, MRP-3, Nestin, OLIG2, ART1, ART4, B-cycline, Gli1, Cav-1, Cathepsin B, CD74, E-Cadherin, EphA2/Eck, Fra-1/Fosl 1, GAGE-1, Ganglioside/GD2, GnT-V, β1, 6-N, Ki67, Ku70/80, PROX1, PSCA, SOX10, SOX11, Survivin, βhCG, WT1, mesothelin, melan-A, NY-BR-1, NY-CO-58, MN (gp250), telomerase, SSX-2, PRAME, PLK1, VEGF-A, VEGFR2, and Tie-2.

In some embodiments, the anti-TEM1 antibodies and antigen-binding portions thereof further comprise one or more antigen-binding portions directed at a T-cell (or other effector immune cell) antigen, including, but not limited to CD3, CD2, CD5, TCRα, TCRβ, CD28, 4-1BB, OX40, GITR, CD16, NKG2D, CD47, and SIRPα.

Also provided herein are antigen-binding antibody portions comprising minimal antigen recognition units consisting of the amino acid residues that mimic the hypervariable region of an antibody (e.g., an isolated CDR such as a CDR3 peptide), or a constrained FR3-CDR3-FR4 peptide.

Provided herein are anti-TEM1 antibodies or antigen-binding portions thereof, as well as methods of using those anti-TEM1 antibodies or antigen-binding portions thereof, wherein the anti-TEM1 antibody is a chimeric, humanized, or human antibody.

As used herein, a "chimeric antibody" refers to a polypeptide comprising at least the antigen-binding portion of an antibody molecule linked to at least part of another protein.

As used herein, a "humanized antibody" refers to an antibody with a framework region having substantially the amino acid sequence of a human immunoglobulin and a CDR having substantially the amino acid sequence of a non-human immunoglobulin (the "import" sequences). In certain embodiments, humanization of an antibody can reduce immunogenicity. In certain embodiments, the frameworks of the humanized antibody are a composite of two or more human antibodies. In other embodiments, surface-exposed framework residues of the antibody are replaced with framework residues of a human antibody to form a humanized antibody. In a preferred embodiment, the frameworks are selected to minimize the presence of amino acid sequences predicted to be T-cell epitopes over a wide population range.

As used herein, the term "human antibody" refers to an antibody having variable and constant regions derived from human germline immunoglobulin sequences. The human antibodies provided herein may nonetheless include amino acid residues not encoded by human germline immunoglobulin sequences (e.g., mutations introduced by random or site-specific mutagenesis in vitro or by somatic mutation in vivo), for example in the CDRs and in particular CDR3.

Provided herein are further other engineered anti-TEM1 molecules, such as domain-specific antibodies, single domain antibodies, domain-deleted antibodies, diabodies, triabodies, tetrabodies, minibodies, nanobodies (e.g., monovalent nanobodies, bivalent nanobodies, etc.), small modular immunopharmaceuticals (SMIPs), and shark variable immunoglobulin new antigen receipt (IgNAR) domains.

In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:16; HCDR2 comprises the amino acid sequence of SEQ ID NO:17; HCDR3 comprises the amino acid sequence of SEQ ID NO: 18; LCDR1 comprises the amino acid sequence of SEQ ID NO:11; LCDR2 comprises the amino acid sequence SNN; and LCDR3 comprises the amino acid sequence of SEQ ID NO: 13. In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:19; HCDR2 comprises the amino acid sequence of SEQ ID NO:20; HCDR3 comprises the amino acid sequence of SEQ ID NO:21; LCDR1 comprises the amino acid sequence of SEQ ID NO:14; LCDR2 comprises the amino acid sequence of SEQ ID NO:15; and LCDR3 comprises the amino acid sequence of SEQ ID NO:13.

In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:4. In one embodiment, the anti-TEM1 antibody or antigen-binding portion thereof comprises a light chain variable region comprising a sequence that is at least 85%, at least 90%, at least 95%, at least 96%, at least 97%, at least 98%, or at least 99%, identical to SEQ ID NO:3. In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:4 and comprises a light chain variable region comprising a sequence that is at least 85% at least 90%, at least 95%, at least 96%, at least 97%, at least 98%, or at least 99%, identical to SEQ ID NO:3. In one embodiment, the anti-TEM1 antibody or antigen-binding portion thereof comprises a heavy chain variable region comprising the sequence of SEQ ID NO:4. In one embodiment, the anti-TEM1 antibody or antigen-binding portion thereof comprises a light chain variable region comprising the sequence of SEQ ID NO:3. In one embodiment, the anti-TEM1 antibody or antigen-binding portion thereof comprises a heavy chain variable region comprising the sequence of SEQ ID NO:4 and a light chain variable region comprising the sequence of SEQ ID NO:3.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only (i) by conservative amino acid substitutions, for example, substitution of one amino acid for another of the same class (e.g., valine for glycine, arginine for lysine, etc.) or (ii) by one or more non-conservative substitutions, deletions, or insertions located at positions of the amino acid sequence which do not destroy the function of the protein. Preferably, the amino acid sequence is at least 80%, at least 85%, at least 90%, at least 95%, at least 96%, at least 97%, at least 98%, or at least 99% similar to another amino acid sequence. Methods and computer programs for determining sequence similarity are publically available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:16; HCDR2 comprises the amino acid sequence of SEQ ID NO:17; HCDR3 comprises the amino acid sequence of SEQ ID NO:22; LCDR1 comprises the amino acid sequence of SEQ ID NO:11; LCDR2 comprises the amino acid sequence SNN; and LCDR3 comprises the amino acid sequence of SEQ ID NO: 13. In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:19; HCDR2 comprises the amino acid sequence of SEQ ID NO:20; HCDR3 comprises the amino acid sequence of SEQ ID NO:48; LCDR1 comprises the amino acid sequence of SEQ ID NO:14; LCDR2 comprises the amino acid sequence of SEQ ID NO:15; and LCDR3 comprises the amino acid sequence of SEQ ID NO:13.

In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:6. In one embodiment, the anti-TEM1 antibody or antigen-binding portion thereof comprises a light chain variable region comprising a sequence that is at least 85%, at least 90%, at least 95%, at least 96%, at least 97%, at least 98%, or at least 99%, identical to SEQ ID NO:5. In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:6 and comprises a light chain variable region comprising a sequence that is at least 85% at least 90%, at least 95%, at least 96%, at least 97%, at least 98%, or at least 99%, identical to SEQ ID NO:5. In one embodiment, the anti-TEM1 antibody or antigen-binding portion thereof comprises a heavy chain variable region comprising the sequence of SEQ ID NO:6. In one embodiment, the anti-TEM1 antibody or antigen-binding portion thereof comprises a light chain variable region comprising the sequence of SEQ ID NO:5. In one embodiment, the anti-TEM1 antibody or antigen-binding portion thereof comprises a heavy chain variable region comprising the sequence of SEQ ID NO:6 and a light chain variable region comprising the sequence of SEQ ID NO:5.

In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:28; HCDR2 comprises the amino acid sequence of SEQ ID NO:29; HCDR3 comprises the amino acid sequence of SEQ ID NO:30; LCDR1 comprises the amino acid sequence of SEQ ID NO:23; LCDR2 comprises the amino acid sequence DAS; and LCDR3 comprises the amino acid sequence of SEQ ID NO:25. In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:31; HCDR2 comprises the amino acid sequence of SEQ ID NO:32; HCDR3 comprises the amino acid sequence of SEQ ID NO:33; LCDR1 comprises the amino acid sequence of SEQ ID NO:26; LCDR2 comprises the amino acid sequence of SEQ ID NO:27; and LCDR3 comprises the amino acid sequence of SEQ ID NO:25.

In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:8. In one embodiment, the anti-TEM1 antibody or antigen-binding portion thereof comprises a light chain variable region comprising a sequence that is at least 85%, at least 90%, at least 95%, at least 96%, at least 97%, at least 98%, or at least 99%, identical to SEQ ID NO:7. In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:8 and comprises a light chain variable region comprising a sequence that is at least 85% at least 90%, at least 95%, at least 96%, at least 97%, at least 98%, or at least 99%, identical to SEQ ID NO:7. In one embodiment, the anti-TEM1 antibody or antigen-binding portion thereof comprises a heavy chain variable region comprising the sequence of SEQ ID NO:8. In one embodiment, the anti-TEM1 antibody or antigen-binding portion thereof comprises a light chain variable region comprising the sequence of SEQ ID NO:7. In one embodiment, the anti-TEM1 antibody or antigen-binding portion thereof comprises a heavy chain variable region comprising the sequence of SEQ ID NO:8 and a light chain variable region comprising the sequence of SEQ ID NO:7.

In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:39; HCDR2 comprises the amino acid sequence of SEQ ID NO:40; HCDR3 comprises the amino acid sequence of SEQ ID NO:41; LCDR1 comprises the amino acid sequence of SEQ ID NO:34; LCDR2 comprises the amino acid sequence STY; and LCDR3 comprises the amino acid sequence of SEQ ID NO:36. In one embodiment, the anti-TEM1 antibody or antigen-binding portion thereof comprises three heavy chain CDRs (HCDR1, HCDR2 and HCDR3) and three light chain CDRs (LCDR1, LCDR2 and LCDR3), wherein HCDR1 comprises the amino acid sequence of SEQ ID NO:42; HCDR2 comprises the amino acid sequence of SEQ ID NO:43; HCDR3 comprises the amino acid sequence of SEQ ID NO:49; LCDR1 comprises the amino acid sequence of SEQ ID NO:37; LCDR2 comprises the amino acid sequence of SEQ ID NO:38; and LCDR3 comprises the amino acid sequence of SEQ ID NO:36.

In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:10. In one embodiment, the anti-TEM1 antibody or antigen-binding portion thereof comprises a light chain variable region comprising a sequence that is at least 85%, at least 90%, at least 95%, at least 96%, at least 97%, at least 98%, or at least 99%, identical to SEQ ID NO:9. In one embodiment, the anti-TEM1 antibody or antigen-binding portion thereof comprises a heavy chain variable region comprising a sequence that is at least 85%, at least 90%, at least 95%, at least 96%, at least 97%, at least 98%, or at least 99%, identical to SEQ ID NO:10 and comprises a light chain variable region comprising a sequence that is at least 85% at least 90%, at least 95%, at least 96%, at least 97%, at least 98%, or at least 99%, identical to SEQ ID NO:9. In one embodiment, the anti-TEM1 antibody or antigen-binding portion thereof comprises a heavy chain variable region comprising the sequence of SEQ ID NO: 10. In one embodiment, the anti-TEM1 antibody or antigen-binding portion thereof comprises a light chain variable region comprising the sequence of SEQ ID NO:9. In one embodiment, the anti-TEM1 antibody or antigen-binding portion thereof comprises a heavy chain variable region comprising the sequence of SEQ ID NO:10 and a light chain variable region comprising the sequence of SEQ ID NO:9.

In one embodiment, the anti-TEM1 antibody or antigen-binding portion thereof comprises a CDR that has one, two, three or more amino acid substitutions as compared to any of the CDR sequences closed herein.

Nucleic Acids

Also provided herein are nucleic acids encoding anti-TEM1 antibodies and antigen-binding portions thereof, as well as vectors, host cells, and expression systems.

The term "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

The nucleic acids encoding anti-TEM1 antibodies and antigen-binding portions thereof may be, e.g., DNA, cDNA, RNA, synthetically produced DNA or RNA, or a recombinantly produced chimeric nucleic acid molecule comprising any of those polynucleotides either alone or in combination. For example, provided is an expression vector comprising a polynucleotide sequence encoding an anti-TEM1 antibodies and antigen-binding portions thereof described herein operably linked to expression control sequences suitable for expression in a eukaryotic and/or prokaryotic host cell.

The term "vector" refers to a nucleic acid molecule capable of transporting another nucleic acid to which it has been linked. A "vector" includes, but is not limited to, a viral vector, a plasmid, a RNA vector or a linear or circular DNA or RNA molecule which may consists of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adeno associated viruses, AAV), coronavirus, negative strand RNA viruses such as orthomyxovirus (e.g., influenza virus), rhabdovirus (e. g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, and spumavirus.

A variety of expression vectors have been developed for the efficient synthesis of antibodies and antigen-binding portions thereof in prokaryotic cells such as bacteria and in eukaryotic systems, including but not limited to yeast and mammalian cell culture systems have been developed. The vectors can comprise segments of chromosomal, non-chromosomal and synthetic DNA sequences. Also provided are cells comprising expression vectors for the expression of the anti-TEM1 antibodies and antigen-binding portions thereof disclosed herein.

In one embodiment, the nucleic acid molecule comprises a sequence encoding any of the sequences of SEQ ID NOS:3-10.

Also provided are vectors and pairs of vectors comprising the nucleic acid molecules disclosed herein, as well as cells comprising such vectors.

Methods of Treatment

In one aspect, the invention provides for anti-TEM1 antibodies and antigen binding portions thereof that are also useful for the treatment of subjects in need thereof.

In the methods described herein, a therapeutically effective amount of an antibody or antigen-binding portions thereof set forth herein is administered to a mammal in need thereof. Although antibodies or antigen-binding portions thereof set forth herein are particularly useful for administration to humans and canines, they may be administered to other mammals as well. The term "mammal" as used herein is intended to include, but is not limited to, humans, laboratory animals, domestic pets and farm animals. "Therapeutically effective amount" means an amount of antibody or antigen-binding portions thereof set forth herein that, when administered to a mammal, is effective in producing the desired therapeutic effect.

As such, also provided herein are methods of treating a subject having a cancer or tumor and/or reducing tumor growth, comprising administering an effective amount of an anti-TEM1 or antigen-binding portion thereof provided herein. "Reducing" includes inhibiting and/or reversing and can refer to, for example, the symptoms of the disorder being treated, the presence or size of metastases or micrometastases, the size of the primary tumor, the presence or the size of the dormant tumor.

The term "cancer" refers to or describes the physiological condition in mammals that is typically characterized by unregulated cell growth. Included in this definition are benign and malignant cancers, as well as dormant tumors or micrometastases. Accordingly, the term "cancer" as used herein refers to an uncontrolled growth of cells, which interferes with the normal functioning of the bodily organs and systems, including cancer stem cells and tumor vascular niches. A subject that has a cancer is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

By "subject" is meant a mammal, including, but not limited to, a human or non-human mam-mal, such as a bovine, equine, canine, ovine, or feline, etc. Individuals and patients are also subjects herein.

The terms "treat," "treated," "treating," or "treatment" as used herein refer to therapeutic treatment measures, wherein the object is to slow down (lessen) an undesired physiological condition, disorder or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The embodiments of the invention may be used for treating metastasis, which relates to the spreading of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers that may be treated by the compositions and methods contemplated by the invention include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated include, but are not limited to benign and malignant tumors, and malignancies e.g., sarcomas, carcinomas, and melanomas. Adult tumors/cancers and pediatric tumors/cancers are also included. Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. A patient can have more than one type of cancer.

In a preferred embodiment, the anti-TEM1 antibodies or antigen-binding portions thereof are used in a method of treating sarcoma, including, but not limited to sarcoma subtypes synovial sarcoma, fibrosarcoma, malignant fibrous histiocytoma (MFH), liposarcoma, and osteosarcoma. In another preferred embodiment, the anti-TEM1 antibodies or antigen binding fragments are used in a method of treating carcinoma, including bladder cancer.

The efficacy of the treatment methods for cancer comprising therapeutic formulations of the compositions comprising the antibodies and antigen binding portions thereof described herein can be measured by various endpoints commonly used in evaluating cancer treatments, including but not limited to, tumor regression, tumor weight or size shrinkage, time to progression, duration of survival, progression free survival, overall response rate, duration of response, and quality of life. In the case of cancers, the therapeutically effective amount of the recombinant anti-TEM1 or antigen-binding portion thereof can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. In cases where a patient has more than one type of cancer, the therapeutically effective amount of the recombinant anti-TEM1 or antigen-binding portion thereof is an amount effective in treating at least one of the cancers. To the extent the anti-TEM1 antibody or antigen-binding portion thereof acts to prevent growth and/or kill existing cancer cells, it can be cytostatic and/or cytotoxic. For cancer therapy, efficacy in vivo can, for ex-ample, be measured by assessing the duration of survival, duration of progression free survival (PFS), the response rates (RR), duration of response, and/or quality of life.

In some embodiments, the anti-TEM1 antibody or antigen-binding portion thereof is administered with a checkpoint inhibitor. Checkpoint proteins interact with specific ligands that send a signal into the T-cell and switch off or inhibit T-cell function. By expressing high levels of checkpoint proteins on their surface, cancer cells can control the function of T-cells that enter the tumor microenvironment, thus suppressing the anticancer immune response. The immune checkpoint protein Programmed Death-1 (PD-1) is a key immune checkpoint receptor ex-pressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T-cell activation and cytokine secretion upon binding to PD-1 (Freeman et al., 2000; Latchman et al., 2001). Inhibition of the PD-1/PD-L1 interaction can promote potent antitumor activity. Examples of PD-1 inhibitors include, but are not limited to, Pembrolizumab (MK-3475), Nivolumab (MDX-1106), Cemiplimab-rwlc (REGN2810), Pidilizumab (CT-011), Spartalizumab (PDR001), tislelizumab (BGB-A317), PF-06801591, AK105, BCD-100, BI 754091, JS001, LZM009, MEDI0680, MGA012, Sym021, TSR-042. Examples of PD-L1 inhibitors include, but are not limited to, Atezolizumab (MPDL3280A), Durvalumab (MEDI4736), Avelumab (MSB0010718C), BGB-A333, CK-301, CS1001, FAZ053, KN035, MDX-1105, MSB2311, SHR-1316.

Further provided are pharmaceutical compositions comprising one or more of the anti-TEM1 antibodies and antigen-binding portions thereof provided herein and a pharmaceutically acceptable excipient.

Diagnostic Methods

The anti-TEM1 antibodies and antigen-binding portions thereof provided herein are also useful for diagnostic purposes. As such, also provided herein are methods of selecting a subject for treatment with an anti-TEM1 antibody or antigen-binding portion thereof, the method comprising contacting a sample from a patient with an anti-TEM1 antibody or antigen-binding portion thereof disclosed herein, and determining the presence of TEM1 in the sample. In some embodiments, the method further comprises administering to the patient anti-TEM1 antibody or antigen-binding portion thereof if TEM1 was determined to be present in the sample. In some embodiments, the sample is a tissue, blood, or a tumor sample.

In some embodiments, the anti-TEM1 antibodies and antigen-binding portions thereof provided herein are used for the identification and/or isolation of cancer cells.

Targeting Methods

The anti-TEM1 antibodies and antigen-binding portions thereof provided herein are also useful for targeting a payload to a cell expressing TEM1. In one embodiment, provided is a method of treating and/or preventing a disease in a subject in need thereof, the method comprising administering to the subject an effective amount of one or more anti-TEM1 antibodies or antigen-binding portions thereof, wherein at least one anti-TEM1 antibody or antigen-binding portions thereof is conjugated to a therapeutic moiety.

Examples of therapeutic moieties which are useful in the methods and antibodies and antigen binding portions thereof contemplated by the invention include, for example, anti-inflammatory agents, anti-cancer agents, anti-neurodegenerative agents, anti-infective agents, or generally a therapeutic. The functional moiety may also have one or more of the above-mentioned functions.

Exemplary therapeutic moieties include radionuclides with high-energy ionizing radiation that are capable of causing multiple strand breaks in nuclear DNA, and therefore suitable for inducing cell death (e.g., of a cancer). Exemplary high-energy radionuclides include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. These isotopes typically produce high-energy α- or β-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutic moieties also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutic moieties also include alkylating agents such as the anthracycline family of drugs (e.g., adriamycin, carminomycin, cyclosporin-A, chloroquine, methopterin, mithramycin, porfiromycin, streptonigrin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum(II) dichloride (cisplatin), melphalan, mitoxantrone, and oxaliplatin.

Exemplary therapeutic moieties also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazylquinone, indoloquinone EO9, diaziridinyl-benzoquinone methyl DZQ, triethylenephosphoramide, and nitrosourea compounds (e.g. carmustine, lomustine, semustine).

Exemplary therapeutic moieties also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and *vinca* alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (+)-thalidomide.

Exemplary therapeutic moieties also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminoglutethimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutic moieties also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary therapeutic moieties also include gene regulators such as 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutic moieties also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), pyrrolobenzodiazepine (PBD) dimers, neocarzinostatin, topotecan, taxanes, cytochalasin B, ethidium bromide, emetine, tenoposide, colchicine, dihydroxy anthracendione, mitoxantrone, procaine, tetracaine, lidocaine, propranolol, puromycin, and analogs or homologs thereof. Any of these cytotoxins can be conjugated to the anti-TEM1 antibody through cleavable or non-cleavable linkers, the choice of which depends on target and target cell and tissue.

In one embodiment, the therapeutic moiety is an immune cell engager, including but not limited to a T-cell, NK cell, and/or macrophage engager. In one embodiment, the therapeutic moiety is a bi-specific T-cell engager (BiTE), which forms a bridge between a cytotoxic T-cell and a tumor cell. In some embodiments, the therapeutic moiety is a cytokine, a chemokine, an interleukin, or an immunomodulatory imide drug. In addition, other molecules that alter the tumor microenvironment in order to increase an immune response against a tumor could be conjugated to the anti-TEM1 antibody, for example a STING agonists such as diABZI.

In one embodiment, the therapeutic moiety is a checkpoint inhibitor.

In some embodiments, the anti-TEM1 antibody or antigen-binding portion thereof is conjugated to a detectable moiety. In some embodiments, the detectable moiety is fluorescent. In some embodiments, the anti-TEM1 antibody or antigen-binding portion thereof is conjugated to an affinity tag and/or a purification tag or molecule. In some embodiments, the anti-TEM1 antibody or antigen-binding portion thereof is conjugated to a magnetic moiety.

It is to be understood that this invention is not limited to the particular molecules, compositions, methodologies, or protocols described, as these may vary. Any methods and materials similar or equivalent to those described herein can be used in the practice or testing of embodiments of the present invention. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes those possibilities).

All references, patents and applications cited herein are incorporated herein by reference in their entireties. Furthermore, where a definition or use of a term in a reference, which is incorporated by reference herein is inconsistent or contrary to the definition of that term provided herein, the definition of that term provided herein applies and the definition of that term in the reference does not apply.

To facilitate a better understanding of the present invention, the following examples of specific embodiments are given. The following examples should not be read to limit or define the entire scope of the invention.

EXAMPLES

Example 1: Selection of Anti-TEM scFvs Using Phage Display scFvs selectively binding to the extracellular domain (ECD) of tumor endothelial marker 1 (TEM1) were selected using phage display.

Phage Display Selections

All phage display selections were carried out using two large, fully human scFv libraries (CHV101_DMk and CHV101_DMl; SMD) constructed from the peripheral blood of 120 healthy volunteer donors. Briefly, IgD/IgM VH, and Vk/Vl domain repertoires were amplified from cDNA prepared from mRNA affinity-purified from enriched CD19$^+$ cells, using a newly designed primer panel. Amplicons were pooled, purified and cloned sequentially (Vk/Vl followed by VH) into the gIII display cassette of a newly designed phagemid vector (pCHV101; SMD). A bacterial library of ~2×10$^{10}$ colonies was generated following electroporation into E. coli TG1 cells. Phage library rescue was performed according to standard published procedures and single-use phage aliquots were stored in a stabilization buffer at −80° C.

Two solid-phase targets were used for phage display selections: (1) streptavidin magnetic beads pre-coated with biotinylated SpyTag (bSpyT), which were further coated with a fusion protein comprising SpyCatcher (SpyC) and the ECD of TEM1 and (2) streptavidin magnetic beads coated directly with purified and biotinylated h/mTEM1 ECD. SpyT is a peptide that can quickly form an amide bond to its protein partner SpyC, allowing quick immobilization of SpyC fusion proteins.

The scFv phage libraries were first blocked with PBST containing 2% skimmed milk, 1% BSA for 30 min at RT, and then incubated for 30 min with streptavidin beads coated only with SpyC domain to subtract ('de-select') non-specific or SpyC-specific binders. Subsequently, blocked and deselected phage particles were transferred to tubes containing similarly blocked SpyC-antigen beads, and incubation was continued at RT for 1 h. Non-binding phage were removed by 5×1 ml washes with PBST followed by 1×1 ml PBS. Typically, the stringency of selection was increased at the second round by transferring the 5×1 ml PBST washed beads into a Falcon tube containing 50 ml PBST and allowing lower affinity phage to passively dissociate over 20 min prior to rapid magnetic capture and final washing with 1 ml 1×PBS. Bound phage were eluted from the beads with 200 µl of 20 µg/ml trypsin (Sigma Aldrich, #T1426) in PBS for 30 min at 37° C. (stationary). Eluted phage were allowed to infect minimal medium-grown E. coli TG1 cells grown to an OD600 of 0.4-0.5 in 10 ml of 2TY medium supplemented with 2% glucose (2TYG) for 1 h at 37° C. (stationary). The infected cells were collected by centrifugation at 4000 rpm (RT), resuspended in 3 ml 2TYG, and plated on 2TYA (ampicillin)G agar with incubation at 30° C. for 18-20 h. Colonies were scraped from plates and the cells stored frozen in 2TYG containing 15% glycerol pending further rounds of phage rescue and selection. Phage rescue between rounds was performed according to standard protocols using M13KO7 helper phage (Life Technologies, #18311019) added at a MOI of 5:1. Secreted phage were collected and purified by two rounds of PEG/NaCl precipitation according to standard protocols, and stored as frozen, single-use aliquots in a stabilization buffer. Clones were cultured for primary screening by picking individual colonies into 2TYAG liquid medium, growing until turbid and then inoculating cells into supplemented TB medium for the induction of protein expression as described above. Clones of interest were subjected to affinity maturation.

Example 2: Affinity Maturation of Anti-TEM1 Clone Candidates

Affinity maturation of selected scFvs was performed to identify high-affinity anti-TEM1 antibodies and antigen-binding portions thereof that are cross-reactive binders and bind to both human and murine TEM1 ECD.

Affinity Maturation and Selection of High-Affinity Binders

Selected scFv clones from Example 1 were subjected to random mutagenesis across the whole scFv, using error-prone PCR with the Diversify PCR random mutagenesis kit (Takara, #630703). The scFv was amplified in one, two or three subsequent rounds of PCR with 25 cycles in the presence of 640 µM MnSO4 and 40 µM dGTP in order to generate variants with low, intermediate and high mutational load. Mutated scFv library DNA was cloned into pCHV101 and electroporated into E. coli TG1 cells to generate libraries of ~$10^9$ colonies. Phage particles displaying the mutagenized scFv libraries were rescued and PEG/NaCl-precipitated before being used in high-stringency affinity maturation selections using purified biotinylated TEM1 (bio-TEM1). In order to enrich for high-affinity, cross-reactive binders towards both human and murine TEM1 ECD, the first round of selection was performed against bead-immobilized bio-hTEM1 and the second round against bio-mTEM1. Both rounds included competition ('off-rate selection') with 200 nM free unlabelled antigen and an extended high-volume washing step of 50 ml PBST (30 min for R1 and overnight for R2). Random colonies were picked from the R2 selection output and sequenced to assess clone integrity and diversity prior to the initiation of screening.

Example 3: Analysis of scFv Binding to TEM1 ECD Using ELISA

The binding of the selected scFvs to SpyC-TEM1 ECD fusion proteins was assessed by enzyme-linked immunosorbent assay (ELISA).

ELISA Binding Assays

Wash steps were performed using 300 ml PBST dispensed from a BioTek™ 405 automatic plate washer. Nunc® Maxisorp™ 96-well plates (Thermo Fisher Scientific, #442404) were coated with 100 ml of 10 mg/ml Neutravidin (Life Technologies, #31000) in PBS overnight at 4° C., washed 3× with PBST and incubated with 100 ml of 1 µM bSpyT peptide in PBS for 1 h at RT with gentle agitation. After blocking in 5% skimmed milk/PBST for 1 h, wells were washed 3× with PBST and 100 µl SpyC-TEM1 ECD expression supernatants (typically diluted 1:10 in PBST+1% BSA for mammalian expression, or blocking buffer for bacterial expression) were added to allow covalent capture by the bound bSpyT. Incubation was at RT for 1.5 h. Wells were washed 4× with PBST and 100 µl blocked scFv culture supernatants added. Wells were washed 4× with PBST and binders were detected using a primary recombinant anti-myc tag antibody (derived from parental mAb clone 9E10, in-house) and a horseradish peroxidase (HRP) conjugated goat anti-mouse IgG antibody (Sigma Aldrich, #A9917). The colorimetric read-out was developed with TMB substrate reagent (Biolegend, #34029) and stabilized with 2 sulfuric acid. Absorbance was measured at 450 nm and 620 nm on a BioTek™ Synergy plate reader. ELISAs were performed in parallel against both cognate SpyC-TEM1 ECD and non-fused SpyC in order to eliminate hits to the latter.

Results scFv candidates 1C1, 1C1mut (an affinity matured variant of 1C1), 2B11, and 3B6 were identified has high-affinity binders using this screen. Their respective CDR, VH, and VL sequences are shown in Tables 1-3.

TABLE 1

Light chain sequences of anti-TEM1 scFvs 1C1, 1C1mut, 2B11, and 3B6. SEQ ID NOs are indicated for amino acid sequences longer than three amino acids.

| | CDR1L | | CDR2L | | CDR3L | | |
| --- | --- | --- | --- | --- | --- | --- | --- |
| | IMGT | Kabat | IMGT | Kabat | IMGT | Kabat | VL |
| 1C1 | 11 | 14 | SNN | 15 | 13 | 13 | 3 |
| 1C1mut | 11 | 14 | SNN | 15 | 13 | 13 | 5 |
| 2B11 | 23 | 26 | DAS | 27 | 25 | 25 | 7 |
| 3B6 | 34 | 37 | STY | 38 | 36 | 36 | 9 |

TABLE 2

Heavy chain sequences of anti-TEM1 scFvs 1C1, 1C1mut, 2B11, and 3B6. SEQ ID NOs are indicated.

| | CDR1H | | CDR2H | | CDR3H | | |
| --- | --- | --- | --- | --- | --- | --- | --- |
| | IMGT | Kabat | IMGT | Kabat | IMGT | Kabat | VH |
| 1C1 | 16 | 19 | 17 | 20 | 18 | 21 | 4 |
| 1C1mut | 16 | 19 | 17 | 20 | 22 | 48 | 6 |
| 2B11 | 28 | 31 | 29 | 32 | 30 | 33 | 8 |
| 3B6 | 39 | 42 | 40 | 43 | 41 | 49 | 10 |

TABLE 3

Variable chain sequences of anti-TEM1 scFvs 1C1, 1C1mut, 2B11, and 3B6.

| SEQ ID NO: | Antibody | VH/VL chain | Amino acid sequence (IMGT designated CDR cores are underlined, Kabat designated CDR cores are bolded) |
|---|---|---|---|
| 3 | 1C1 | VL | QPVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNALVFGGGTKLTVL |
| 4 | 1C1 | VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCASLTSYYGDPTGFDYWGQGTLVTVSS |
| 5 | 1C1mut | VL | QPVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNALVFGGGTKLTVL |
| 6 | 1C1mut | VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCASLISYYGDPTGFDYWGQGTLVTVSS |
| 7 | 2B11 | VL | DIQMTQSPPTLSASVGDRVTITCRASQSISRWLAWYQQKPGKAPNLLIYDASNLQSGVPSRFSGSGSGTEFTLTISSLQPDDFGTYYCQQYKNYSPTFGQGTKLEIK |
| 8 | 2B11 | VH | EVQLVETGGGLVKPGGSLRLSCAASGFTFNTYTMNWVRQAPGKGLEWVSSISSSSTYIYYADSVKGRFTISRDNAKNSLYLQMNSLRAEDTAVYYCAKSIVGATHDAFDIWGQGTMVTVSS |
| 9 | 3B6 | VL | QAVLTQPPSASGTPGQRVTISCSGSSSNIGINTVNWYQQLPGTAPKLLIYSTYQRPSGVPGRFSGSKSATSASLAISGLQSEDEADYYCATWDDSLNGVVFGGGTKLTVL |
| 10 | 3B6 | VH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARVRGSHPWFDPWGQGTLVTVSS |

Example 3: Reformatting of Selected scFvs into scFv-Fc Fusions or T-Cell Engagers Selected scFv candidates (1C1, 2B11, and 3B6) were subcloned into a pTT-based vector containing a vector-encoded human IgG1 constant region to produce scFv-Fc fusion proteins (see FIG. 1A). Alternatively, the selected scFv candidates were fused to an scFv derived from an anti-CD3 antibody (clone UCHT1) to generate secreted T-cell engagers (BiTE).

Production of scFv-Fc Fusion Proteins and BiTE Molecules

Recombinant protein was produced using the mammalian HEK293-6E/pTT transient expression system (National Research Council of Canada; obtained under license). HEK293-6E cells were grown in Freestyle F17 medium (Thermo Fisher Scientific, #A13835) containing 4 mM GlutaMAX (Life Technologies, #35050061), 0.1% Pluronic® F-68 (Life Technologies, #24040032) and 25 µg/mL G418 (Life Technologies, #10131019) at 37° C., 5% $CO_2$ and 120 rpm. For transfection, the DNA was mixed with FectoPRO (Polyplus, #116-010) transfection reagent in F17 medium without supplements, according to the manufacturer's instructions. After five days of protein expression, cultures were subjected to low speed centrifugation and the media collected. Samples could be used immediately for direct capture and immobilization (dCI) selection/assay experiments or snap-frozen and stored at −80° C. until required.

Purification of scFv-Fc Fusion Proteins and BiTE Molecules

ScFv-Fc fusions were purified from clarified expression media using a HiTrap™ MabSelect column (GE Healthcare, #11003494), followed by extensive dialysis against phosphate-buffered saline (PBS). Also purified was sc78-Fc as a positive control. Sc78 is an anti-TEM1 antibody and was previously described in WO2011060233A1.

His-tagged T-cell engagers were purified by IMAC chromatography using a HisTrap™ Excel column (GE Healthcare, #17-3712-05). The peak monomer fractions were pooled and buffer-exchanged into PBS using a Superdex 200 Increase 10/300 GL preparatory grade column (GE Healthcare, #28-9909-44).

Expression of Recombinant Human and Mouse TEM1 for Soluble and Cell-Based Assays Extracellular domain (ECD) fragments of human and mouse TEM1 membrane antigens were synthesized (GeneArt, Thermo Fisher Scientific) based on sequences and predicted topologies obtained from UniprotKB. Gene fragments were either fused N- or C-terminally to vector-encoded CnaB2-derived SpyCatcher (SpyC; Genbank accession: JQ478411.1; amino acids 28-136), or to a 6×his/AviTag motif housed in a pTT-based mammalian episomal expression vector. A semi-synthetic signal peptide was used to target expressed protein for secretion to the medium. The 6×his-tagged variants of human or murine TEM1 ECD containing a C-terminal biotinylation sequence were purified using a HisTrap™ excel column followed by site-directed enzymatic biotinylation using purified BirA.3 Following confirmation of biotinylation by avidin gel shift assay, the proteins were buffer exchanged into PBS supplemented with 0.1% BSA and stored at −80° C. Transient transfection of HEK293T cells with the full length (FL) hTEM1 cDNA ORF (extracted from Genbank RefSeq NM_020404.3) and an irrelevant membrane-localized control ORF (anti-hCD19 2nd generation CAR construct) utilized the pTagGFP2-N CMV promotor vector (Evrogen, #FP192). Briefly, HEK293T cells were detached and plated in 6-well plates at $10^6$ cells/well in a volume of 4 ml. Recombinant plasmid DNA (4 g) was combined with 400 µl serum-free DMEM and 6 µl Turbofect reagent (Life Technologies, #R0532), and incubated for 20 min at RT before being added dropwise to the plated cells. Transfected cells were maintained at 37° C., 5% $CO_2$ under a humidified atmosphere for 48 h. Transient transfection of HEK293-6E with FL-canine TEM1 cloned into pTagGFP2-N was performed using the NCBI Reference Sequence: XM_540833.6. (FIG. 1B).

Example 4: Analysis of scFv-Fc Fusion Binding to Human TEM1 Expressing Cells Using FACS The ability of anti-TEM1 scFv-Fc fusions to bind to TEM1 expressed on cells was assessed using fluorescence-activated cell sorting (FACS).

Adherent cells were detached using 10 mM EDTA, counted and resuspended in fresh, complete culture medium. All subsequent steps were performed on ice. For each sample, $0.5 \times 10^6$ cells were first blocked in FACS buffer (5% FBS in PBS) and then incubated for 1 h with test antibody (typically 1-2 g/ml) or expression supernatant diluted in FACS buffer. After washing three times with FACS buffer, the secondary antibody, Alexa Fluor 647 AffiniPure® Goat Anti-Human IgG (Jackson Immunoresearch, #109-605-098, 1:200 dilution) was added. Following incubation for 30 min the cells were washed again three times. Immediately before data acquisition, dead cells were stained with 4',6-Diamidino-2-phenylindole (DAPI, 1:2000 dilution). Data was acquired using an LSR-II flow cytometer equipped with FACSDIVA software (BD Biosciences). Data analysis and plotting were carried out using FlowJo v10 (FlowJo LLC). As shown in FIG. 2, anti-TEM1 scFv-Fc fusions 1C1, 2B11, and 3B6 bound to TEM1 expressing cell lines, but not to TEM1⁻ control cell lines, demonstrating that the selected scFv-Fc fusions are selective for TEM1. sc78-Fc served as a (TEM1 binding) positive control and was previously described in WO2011060233A1.

Figure 5:
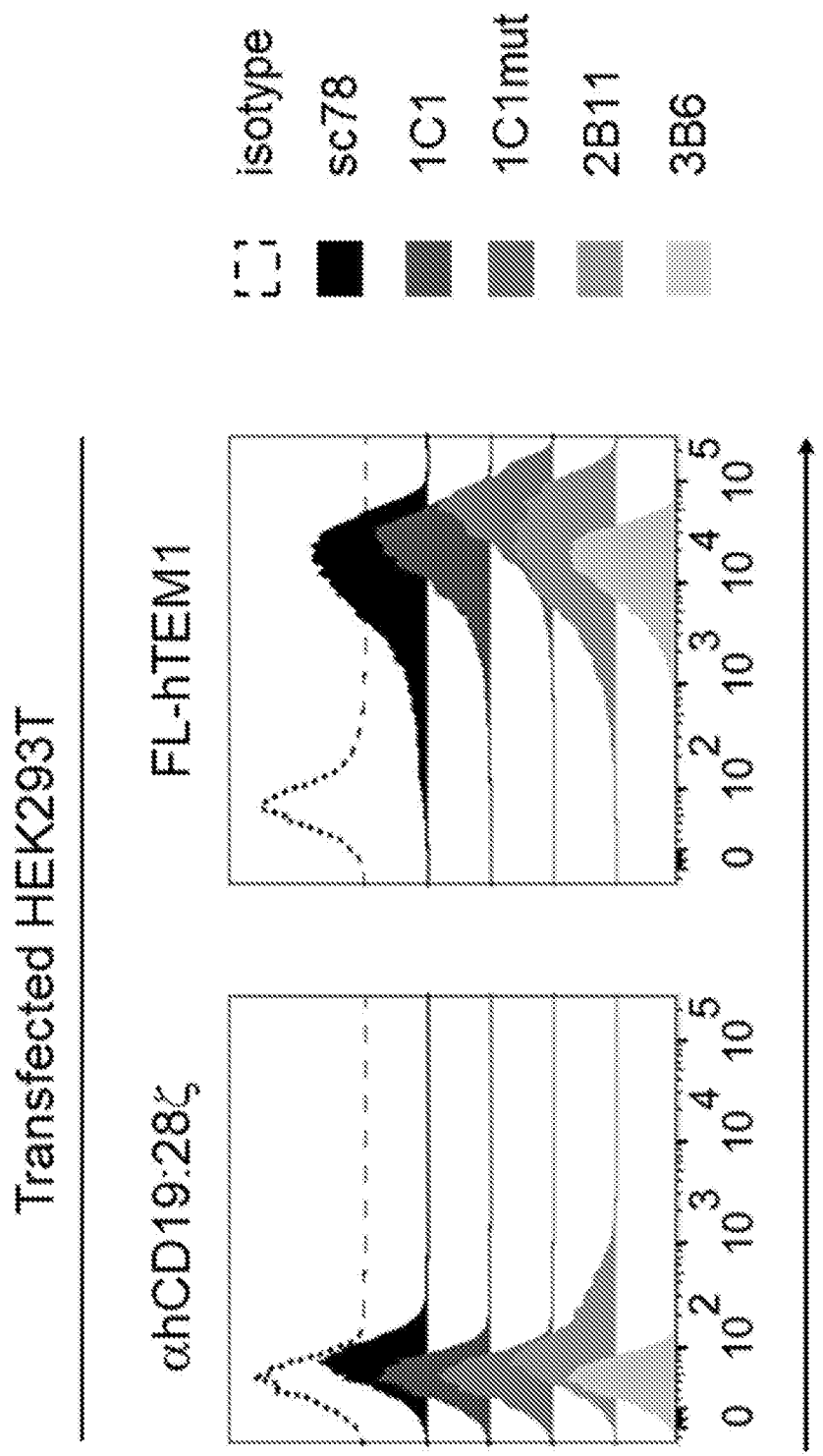
FIG. 5 illustrates the TEM1+ selectivity of 1C1 and 1C1mut. Anti-TEM1 scFv-Fc clones (2 µg/ml) bound to HEK293T cells transiently transfected with native FL-hTEMT (right), but not to cells transfected with an irrelevant cell surface-presented molecule (2nd generation CAR) (left) as determined by FACS.
Figure 7:
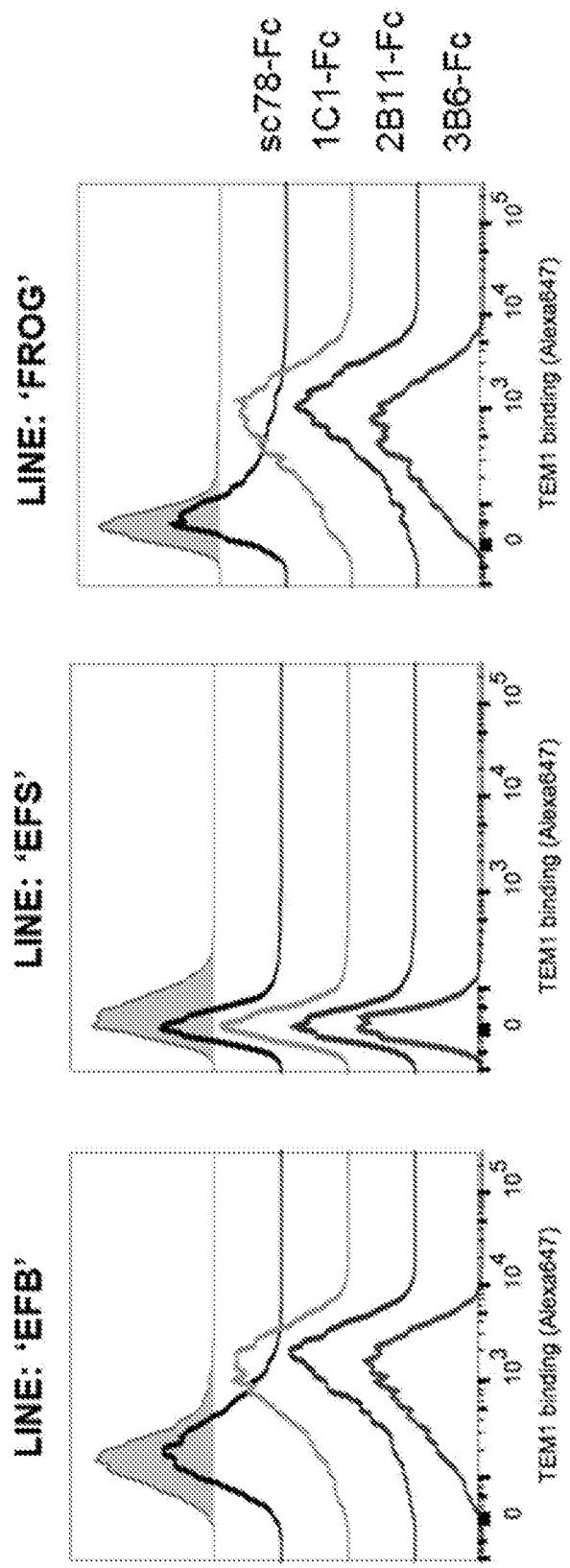
FIG. 7 illustrates that 1C1 effectively recognizes canine TEM1 in the context of endogenously expressing tumor cell lines. Binding of anti-TEM1 scFv-Fc 1C1 clone (0.2 µg/ml) to 2 out of 3 canine hemangiosarcoma tumor cell lines was determined using FACS. EFB is a canine hemangiosarcoma cell line derived from a metastatic brain tumor. EFS and FROG are canine hemangiosarcoma cell lines derived from the spleen.

Similarly, FIG. 5 shows that scFv-Fc fusions 1C1, 1C1 mut (see Example 5), 2B111, and 3B6 bind to cells transiently transfected with native FL-hTEM1, but not to a control cell line.

Example 5: Analysis of scFv-Fc Fusion/T-Cell Engager Binding to Human TEM1 Using Surface Plasmon Resonance (SPR)

The binding of 1C1 and 1C1mut in scFv-Fc fusion and T-cell engager (BiTE) format were determined by surface plasmon resonance (SPR). Bi-specific T-cell engagers (BiTEs) are bispecific monoclonal antibodies that T-cells to cancer cells. BiTEs are fusion proteins comprising a scFv targeting a cancer antigen such as TEM1, and a scFv that binds to T-cells via the CD3 receptor.

SPR

SPR analysis was performed on a Biacore T200 instrument (GE Healthcare). Experiments involving TEM1-SpyC ligand immobilization used a Series S SA sensor chip (GE Healthcare, #BR-1005-31). Briefly, 1 ml of crude TEM1-SpyC expression media was incubated with 1 µM of bSpyT at RT for 2 h with gentle rotation. The resulting covalent TEM1-SpyC:bSpvT complex was separated from free bSpyT by buffer-exchange into 1× e C-A4 Sub AMD filtered Biacore® running buffer (HBS-EP+; 0.01 M HEPES, 0.15 M NaCl, 0.05% Surfactant P20, 3 mM EDTA, pH 7.4; GE Healthcare, #BR-1006-69) using a spin column with a 10 KDa cut-off (VIVASPIN® 6: GE Healthcare #28932296). The biotinylated TEM1-SpyC ligand complex was immobilized-on the SA chip at a density of 150 RU. For kinetic analysis, analytes were diluted into running buffer and injections/dissociations carried out at 30 µl/min with data collected in Single Cycle Kinetics mode. For Fc-capture experiments, 10000 RU of AffiniPure® Goat Anti-Human IgG (Jackson ImmunoResearch, #109-005-098) were immobilized on a CM5 Series S sensor chip (GE Healthcare, #BR-1005-30) by amine coupling according to the manufacturer's instructions. Anti-TEM1 scFv-Fc molecules were captured at a target density of 100 RU and analytes were injected and dissociated at 30 l/min with data acquired in Multiple Cycle Kinetics mode. Surfaces were regenerated between cycles/experiments by injecting 10 mM glycine-HCl, pH 1.5 for 30 s. Corrections for bulk shift and refractive index changes were performed by subtracting the signal of a reference flow cell from the active cell.

Results

Figure 3:
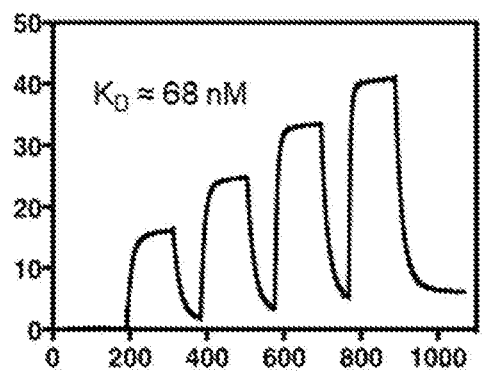
FIG. 3 illustrates the apparent 70-80-fold differential affinity of 1C1 and 1C1mut to human TEM1 using two distinct analyte/ligand Surface Plasmon Resonance (SPR) formats. SPR monovalent affinity determination of parental clone 1C1 (upper sensorgrams) and an affinity-matured variant, 1C1mut (lower sensorgrams), formatted as either a BiTE (left) or a scFv-Fc (right), and using either hTEMT-SpyC (left) or 1C1/1C1mut scFv-Fc (right) as the immobilized ligand. Soluble analyte concentration ranges were 100, 50, 25, 12.5 and 0 nM for 1C1, and 5, 2.5, 1.25, 0.625 and 0 nM for 1C1mut experiments. hTEM1-FL=full-length human TEM1 extracellular domain.
Figure 3:
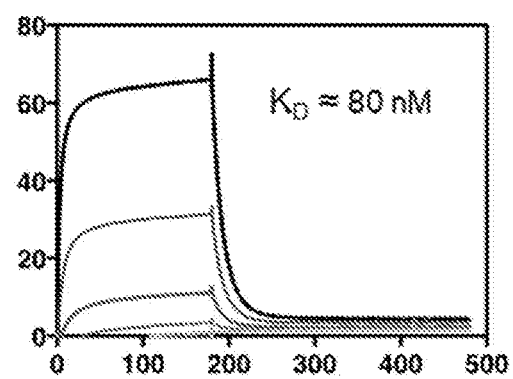
Figure 3:
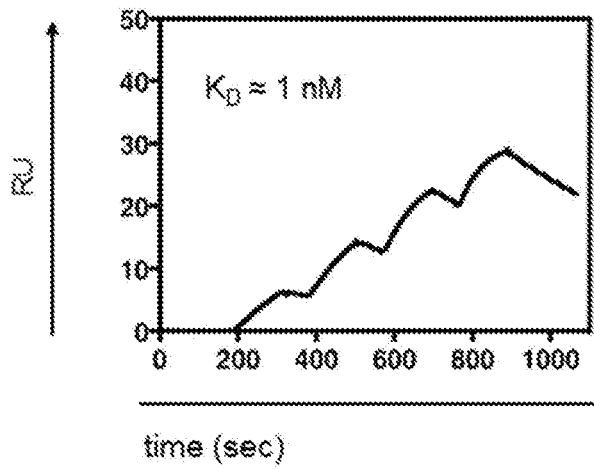
Figure 3:
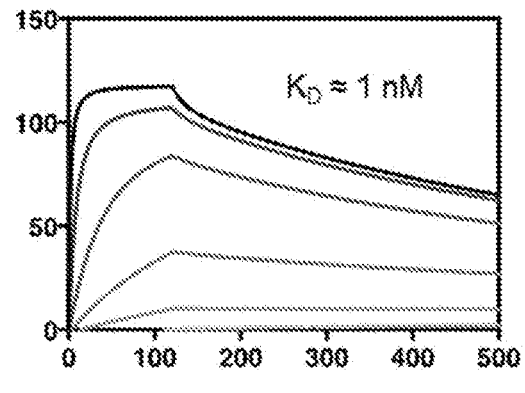

As show in FIG. 3, 1C1mut shows a 70-80 fold increased affinity for human TEM1 in both BiTE as well as scFv-Fc format.

Example 6: Cross-Reactivity of Isolated scFv-Fc Fusions

Figure 4:
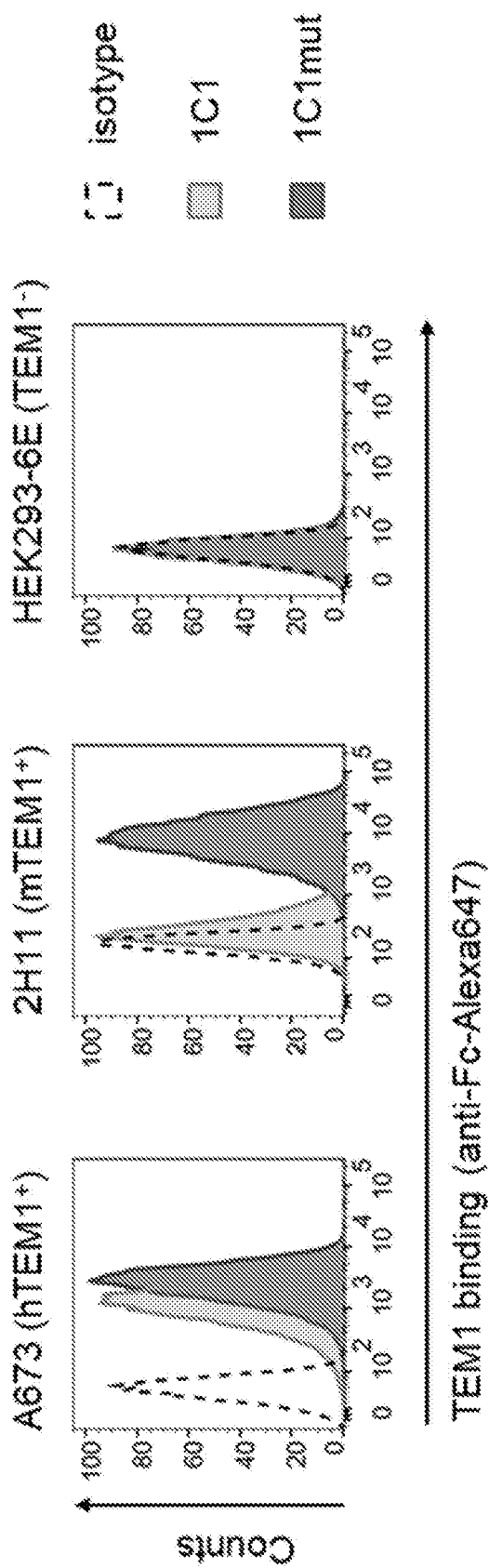
FIG. 4 illustrates that 1C1mut effectively recognizes both human and murine TEM1+ cells. Binding of 1C1mut variant scFv-Fc (0.1 µg/ml) to endogenous human (A673) and murine (2H11) TEM1+ cell lines was determined using FACS. HEK293-6E cells served as TEM1− control cells.

As shown in FIG. 4, 1C1mut recognizes both human and murine TEM1, demonstrating that this antibody may be used in animal studies and can also serve as a therapeutic agent in humans.

As shown in FIGS. 6 and 7, 1C1 binds to cells transiently expressing canine TEM1, as well as to TEM1⁺ canine tumor cells.

Example 7: Generation of TEM1-Binding TriloBiTE (Tri-Lobed Bi-Directional T-Cell Engager) Molecules TriloBiTE molecules were generated by C-terminal fusion of an anti-TEM1 (1C1 and 1C1mut) scFv domain to the VH-CH1 (derived from human IgG1) and VL-Cκ domain of a humanized and chimeric anti-CD3 Fab (derived from clone UCHT1) via a flexible, glycine/serine-rich linker (see FIG. 1C). The resulting constructs are referred to as 1C1-tB (TriloBiTE comprising 1C1 scFv) and 1C1m-tB (TriloBiTE comprising 1C1mut scFv).

Generation of TriloBiTe Constructs

To generate the TriloBiTE constructs, nucleic sequences were synthesized encoding the heavy and light chains of the humanized and chimeric anti-CD3 clone UCHT1 were synthesized in Fab format (GeneArt, Thermo Fisher Scientific) (VH sequence of anti-CD3 antibody: SEQ ID NO:44; VL sequence of anti-CD3 antibody: SEQ ID NO:45). The following, stabilizing mutations were introduced at the CH1-CK interface: S64E and S66V (CH1 domain) and S69L and T71S (Cκ domain). The sequences encoding for the heavy and light chains of the resulting chimeric molecule were separately cloned into a pTT-based mammalian episomal expression vector. Both constructs contained modular cloning sites (NcoI/SalI) to accommodate insertion of the anti-TEM1 scFv encoding sequences. In the resulting TriloBiTE molecules, the scFv fragments were C-terminally fused to the CH1 or CK domain of the anti-CD3 Fab via a flexible, glycine/serine-rich) linker (i.e., GGGGSGGGSGGGS (SEQ ID NO:46) for CK and DKTHTGGGGSGGGS for CH1 (SEQ ID NO:47).
Protein Expression Recombinant protein was produced using the mammalian HEK293-6E/pTT transient expression system (National Research Council of Canada). HEK293-6E cells were grown in Freestyle F17 medium (Thermo Fisher Scientific, #A13835) containing 4 mM GlutaMAX (Life Technologies, #35050061), 0.1% Pluronic® F-68 (Life Technologies, #24040032) and 25 µg/mL G418 (Life Technologies, #10131019) at 37° C., 5% $CO_2$ and 120 rpm. For transfection, the DNA was mixed with FectoPRO (Polyplus, #116-010) transfection reagent in F17 medium without supplements, according to the manufacturer's instructions. After five days of protein expression, cultures were subjected to low speed centrifugation and the media collected.
Protein Purification of TriloBiTEs TriloBiTEs were purified from clarified expression media by immobilized metal ion affinity chromatography (IMAC) using a HisTrap excel column (GE Healthcase, #17371205) at a flow-rate of 1 ml/min. The column was equilibrated with 50 mM Tris, 0.5 M NaCl, 10 mM imidazole, pH 7.5 and protein was eluted with 50 mM Tris, 0.5 M NaCl, 300 mM imidazole, pH 7.4 in 1 ml fractions. Monomeric peak fractions were immediately separated by preparative size-exclusion chromatography using a Superdex 200 Increase 10/300 GL column (GE Healthcare, #28990944) at a flow-rate of 0.75 ml/min. PBS (0.01 M phosphate, 0.14 M NaCl, pH 7.4) was used as sample diluent and eluent. All chromatography experiments were run on an ÄKTApure chromatography system (GE Healthcare).
Biophysical Protein Characterization of Trilobites Purified protein samples were quality controlled by SDS-PAGE. 2 µg purified tB protein were resuspended in 1×LDS buffer (NuPAGE; Life Technologies, #NP0007) with or without 10% reducing agent (NuPAGE; Life Technologies, #NP0009) and heated at 70° C. for 10 min. Samples were separated on a Novex 4-12% Bis-Tris gel (Life Technologies, #NP0321) for 38 min at 200 V and separated protein bands visualized by Coomassie Blue staining (InstantBlue; Expedeon, #ISB1L).

The integrity and homogeneity of tB candidates was assessed by size-exclusion chromatography (SEC) using an AKTApure chromatography system (GE Healthcare). To this end, 100 µl concentrated (~1 mg/ml) protein sample was injected and separated over a Superdex 200 Increase 5/150 GL analytical grade column (GE Healthcare, #28990945) at a flow rate of 0.45 ml/min. PBS (0.01 M phosphate, 0.14 M NaCl, pH 7.4) was used as sample diluent and eluent.

In order to compare the relative thermal stability of different scFv clones, a thermal shift assay was performed following the Protein Thermal Shift Assay protocol from Applied Biosystems (#4461146). Therefore, purified protein was diluted to 5 µM with PBS and mixed with 5 µl Protein Thermal Shift Buffer and 2.5 µl 8× Protein Thermal Shift Dye. Each reaction was prepared in triplicate in a MicroAmp Fast Optical Reaction Plate (Lifetechnologies, #4346907) and sealed with MicroAmp Optical Adhesive Film (Lifetechnologies, #4360954). Melting curves were generated with a 7500 Fast RT-PCR machine (Applied Biosystems), starting at 25° C. and gradually increasing the temperature by 0.05° C./s until reaching 99° C. To obtain relative melting temperatures based on the transition point of the melting curve, the derivative of the fluorescence signal was calculated as a function of temperature. Data analysis was carried out using Applied Biosystems 7500 Fast RT-PCR software.
Results Recombinant expression in HEK293-6E cells followed by affinity chromatography yielded good protein quantities (≈20 mg/l) of the expected size (≈110 kDa). Analyses of protein homogeneity of the purified material by analytical SEC revealed >95% monomeric species for both 1C1-tB and 1C1m-tB. Assessment of thermostability by Differential Scanning Fluorimetry (DSF) revealed melting transitional temperatures comparable to those obtained in the scFv-Fc fusion format: 71.4° C. for 1C1-tB and 64.9° C. for 1C1m-tB.

Example 8: Anti-TEM1 TriloBiTE Molecules Engage and Activate Human T-Cells In Vitro The ability of anti-TEM1 TriloBiTE molecules to specifically engage and activate primary human T-cells, to induce T-cell cytokine secretion, and to induce T-cell cytotoxicity was assessed.
Purification of Primary Human T-Cells For the isolation of primary T-cells, peripheral blood mono-nucleated cells (PBMCs) were isolated from fresh buffy coats obtained from healthy volunteer donors (Service de transfusion, Epalinges, Switzerland). PBMCs were separated by density centrifugation using Lymphoprep (Axonlab, #1114545). Pan-T-cells were subsequently extracted by magnetic separation using a human pan-T-cell isolation kit (Miltenyi Biotec, #130-096-535) and stimulated with human T-cell activator CD3/CD28 beads (Life Technologies, #11161D) and 50 RU IL-2 (Peprotech, #200-02-50UG) for 5 days. After the removal of the beads, primary T-cells were further expanded with IL-7 and IL-15 (Miltenyi Biotec, #130-095-367 and #130-095-765) for a further 5-10 days.
Early T-Cell Activation Assay For measuring early T-cell activation, $0.5 \times 10^6$ A673 (hTEM1') or Raji (hTEM1⁻) target cells were seeded into 24-well plates. Subsequently, $0.5 \times 10^6$ purified and expanded primary human T-cells were added the wells. When used, purified tB protein was added to a final concentration of 5 nM. After 16-18 h of co-culture, the stimulated T-cells were recovered and washed once in FACS buffer. Cells were blocked with FACS buffer (5% FBS, PBS) for 20 min on ice and incubated with the following staining mix: APC anti-hCD8 (Biolegend #344722), BV785 anti-hCD4 (Biolegend #317441), Alexa Fluor 700 anti-hCD69 (Biolegend #310922), PE anti-hCD25 (Biolegend #302606). After 30 min of incubation on ice, the cells were washed again three times. Immediately before data acquisition, dead cells were stained with 4',6-Diamidino-2-phenylindole (DAPI, 1:2000 dilution). Data was acquired using an LSR-II flow cytometer equipped with FACSDIVA software (BD Biosciences). Data analysis and plotting were carried out using FlowJo v10 (FlowJo LLC).
Quantification of IFN-γ Effector Cytokine Supernatants of co-cultures set up as described above were tested for the presence of T-cell-secreted IFN-γ effector cytokine. Quantification was by performed using beads (MultiCyt QBeads, Bucher Biotec #90603). Assays were performed according to the manufacturer's instructions. Standard curves were prepared to quantify secreted cytokine. MultiCyt beads were analyzed on an Intellicyt iQue™ Screener PLUS instrument (10 s sampling; 1 μl/s).

Cytotoxicity Assay (LDH Release)

For T-cell activation assays, $2 \times 10^4$ adherent target cells were seeded in 96-well flat-bottom plates and allowed to attach for ~20 h. When approximately 30% confluency was observed, soluble tBs were added as 3-fold serial dilutions, typically starting from 5 nM. Positive control wells were lysed using 1% Triton X-100. $1.25 \times 10^6$ purified and expanded primary human T-cells were added to the plate to reach an E:T ratio of around 5:1 and incubated for 24 h at 37° C. Specific target cell killing was assessed by measuring LDH release with the CytoTox 96 kit from Promega (#G1780), following the manufacturer's instructions. Control wells were lysed using 10% Triton X-100. Subsequently, 50 μl clarified culture supernatant was mixed with 50 μl CytoTox 96 Reagent and incubated at RT for 30 min (protected from light). The reaction was stopped by adding 50 μl stop solution and LDH activity was quantified colorimetrically, measuring absorbance at 490 nm on a BioTec H1MFG Synergy plate reader. Background signal was subtracted from all samples and corrected cell killing (spontaneous release by targets and effectors subtracted) were calculated as a percentage of maximum lysis.

Real-Time Kinetics of Cell Killing

For the assessment of specific target cell killing using real-time kinetic cell imaging, $2 \times 10^4$ adherent target cells were seeded in 96-well flat-bottom plates and allowed to attach for ~20 h. When approximately 30% confluency was observed, soluble TriloBiTEs were added at a concentration of 0.6 nM or 0.06 nM, respectively. Positive control wells were lysed using 1% Triton X-100. $1.25 \times 10^6$ purified and expanded primary human T-cells were added to the plate to reach an E:T ratio of around 5:1. Cytotox Red reagent (Essen Bioscience, #4632) was added to a final dilution of 1:4000, and resultant cell death was monitored as an increase in fluorescence over time, acquiring images every hour. Image acquisition and data analysis were performed on an Incucyte Live Cell Analysis system (Essen Bioscience).

Results

Figure 8:
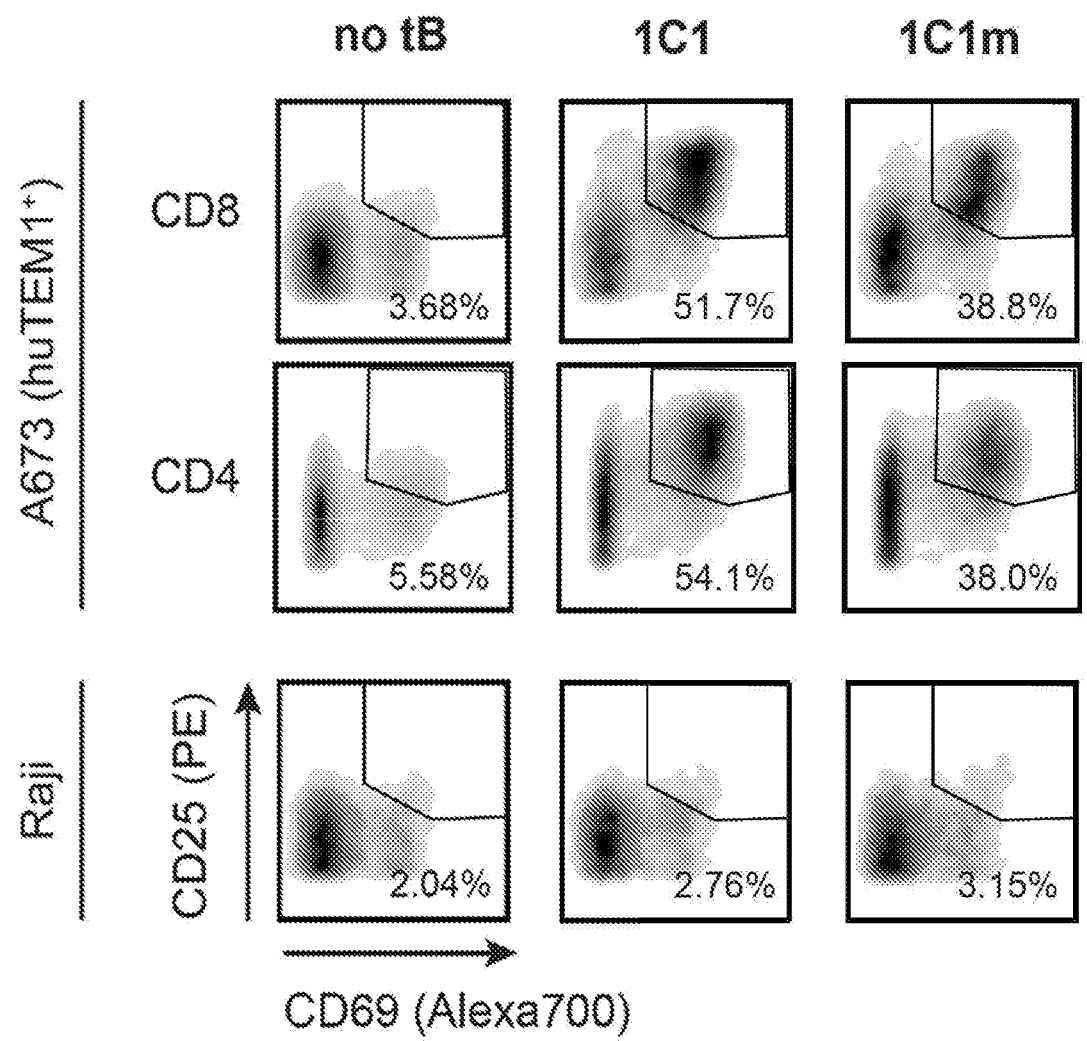
FIG. 8 illustrates that anti-TEM1-TriloBiTEs (tBs) specifically activate both CD8+ and CD4+ primary human T-cells in the presence of TEM1-expressing A673 cells. Upregulation of early activation markers CD69 and CD25 (upper right gate) was measured by flow cytometry after 16 h of co-culture. Expression of CD69/CD25 by CD8+ T-cells co-cultured with Raji cells (TEM1−) is shown as a control.

Co-cultivation of TEM1-expressing A673 cells, human T-cells and either TriloBiTE construct 1C1-tB or 1C1m-tB led to significant early T-cell activation as evidenced by increased T-cell expression of CD69 and CD25, early markers of T-cell activation (FIG. 8). No T-cell activation was observed in presence of hTEM1⁻ Raji cells (FIG. 8).

Figure 9:
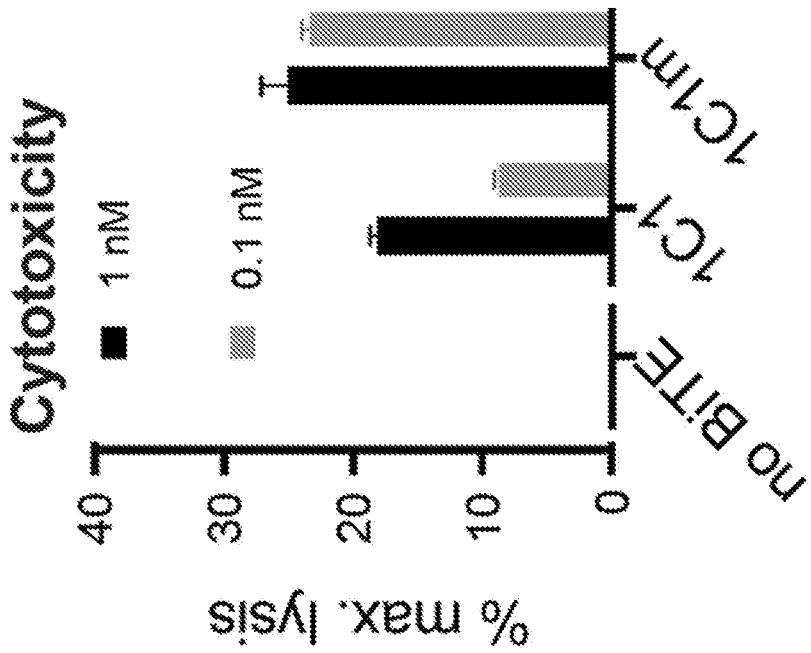
FIG. 9A illustrates IFN-γ secretion by primary human T-cells activated with anti-TEM1 TriloBiTE variants (1 nM) in the presence of different target cell lines: A673 (hTEM1+), SK-N-AS (hTEM1+), and AsPC-1 (hTEM1−). Cytokine concentration in the supernatant was measured after 24 h of co-culture.
FIG. 9B illustrates that anti-TEM1 TriloBiTE molecules redirect primary human T-cells to kill TEM1-expressing A673 cells. TriloBiTEs were added at 1 nM or 0.1 nM and LDH activity was measured after 24 h as a reporter of lysed cells. Specific cell killing was calculated as a percentage of complete lysis achieved with 1% Triton-X 100.
Figure 9:
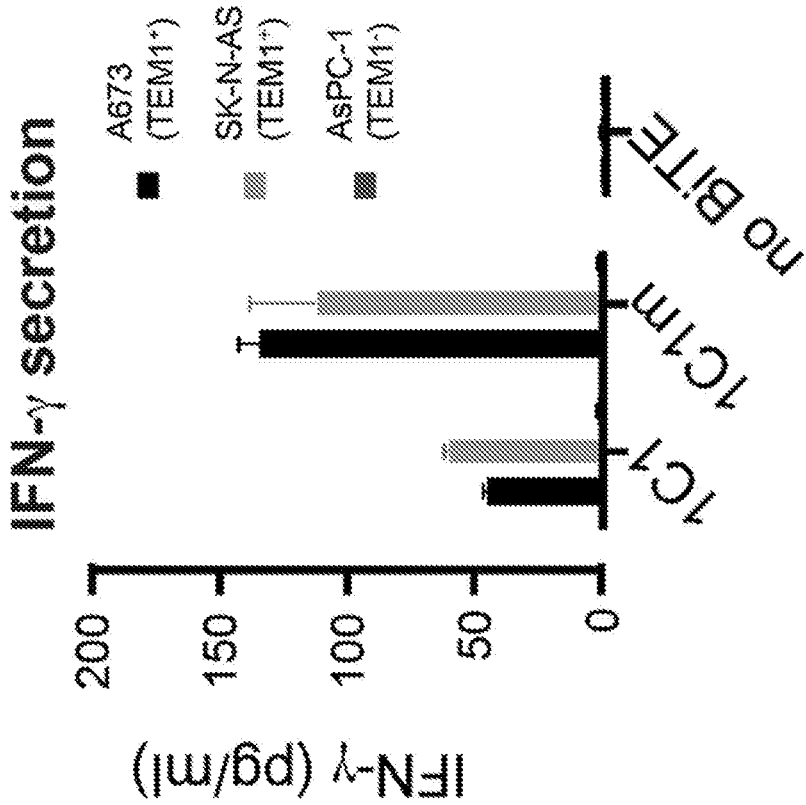

Anti-TEM1 TriloBiTEs stimulated primary human T-cells to secrete IFN-γ effector cytokine and to lyse hTEM1⁺ tumor cells (A673 or SK-N-AS) after 24 h of co-culture (A673 is a human sarcoma cell line, and SK-N-AS is a human neuroblastoma cell line) (FIG. 9). The activation of T-cell effector functions was specific and did not occur in the presence of hTEM1⁻ AsPC-1 cells (human adenocarcinoma cell line). At lower tB concentrations (0.1 nM), the higher-affinity variant 1C1m achieved the lysis of a higher proportion of target cells (FIG. 9).

Figure 10:
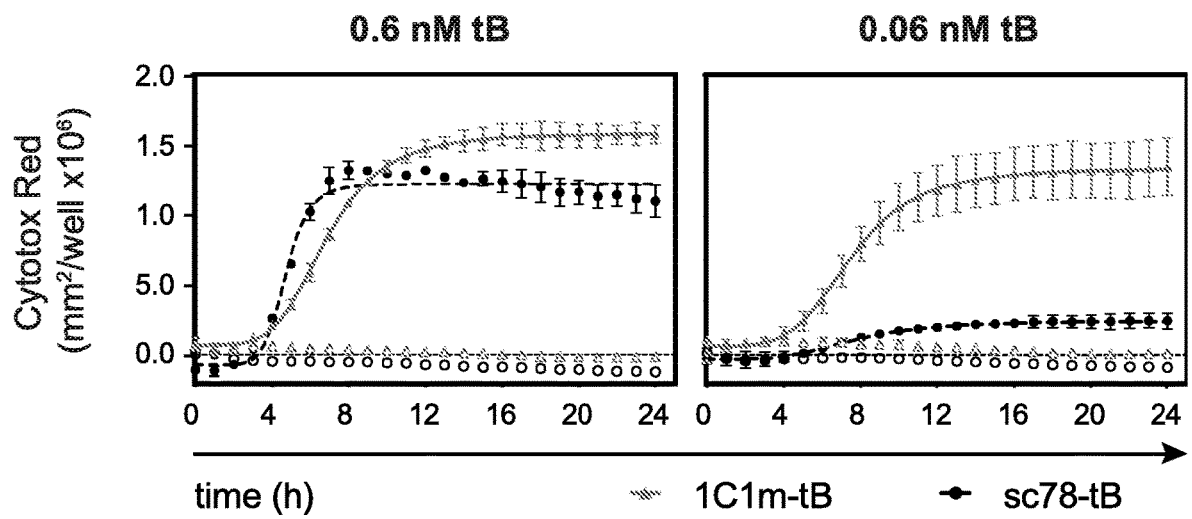
FIG. 10 illustrates real-time kinetics of cell killing by primary human T-cells activated with 0.6 nM or 60 pM 1C1mut or sc78 TriloBiTE. Image-based acquisition of Cytotox Red signal indicates lysis of TEM1+ A673 cells (closed symbols and connected lines), while TEM1-negative AsPC-1 cells (open symbols) are spared.

In a time-lapse microscopy-based killing assay, both 1C1m and the previously published anti-TEM1 scFv sc78 specifically and rapidly redirected primary human T-cells to lyse relevant target cells in the TriloBiTE format. In both cases, complete lysis was reached after 12 h. 1C1m-tB was able to efficiently mediate complete lysis of TEM1-expressing target cells at a ten times lower molecular concentration than sc78-tB. Furthermore, neither of these molecules activated T-cells in the presence of control cells, thereby sparing them from T-cell mediated cytotoxicity (FIG. 10).

Figure 11:
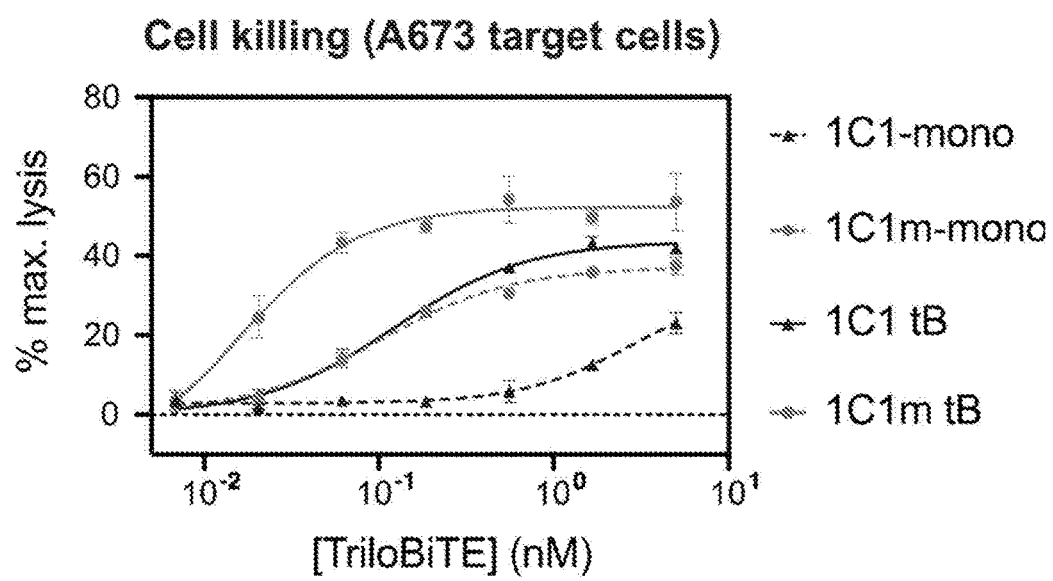
FIG. 11 shows a comparison of different TriloBiTEs (comprising high- or low-affinity scFvs in a mono- or bivalent format) as mediators of cytotoxic T-cell activity. Lysis of hTEM1+ target cells (A673) by polyclonal human T-cells was quantified based on LDH released from dead cells. Cell killing is expressed as a fraction of maximal lysis achieved with 1% Triton-X 100.

To fine-tune TriloBiTE specificity and T-cell engagement, mono- and bi-valent TriloBiTEs of both 1C1 (low-affinity variant) and 1C1mut (high affinity variant) were generated and their respective ability to achieve T-cell induced lysis of hTEM1⁺ cells was examined. As expected, the bivalent TriloBiTE comprising the high affinity scFv (1C1mut) led to the highest degree of target cell killing, whereas the monovalent TriloBiTE comprising the lower affinity scFv (1C1) resulted in the lowest degree of killing (FIG. 11).

Example 9: Anti-TEM1 TriloBiTE Molecules Engage and Activate Human T-Cells In Vivo The ability of a TriloBiTE comprising the 1C1mut-scFv (1C1m-tB) to redirect primary human T-cells to tumor cells in vivo was assessed using a mouse model.

Tumor Growth Assay

For the A673 xenograft study, 30 female NSG mice (10-week old) were implanted with $10^6$ A673 cells s.c. on the right flank. 10 out of the 30 animals received only A673 cells and 20 mice received the tumor cells mixed with $10^7$ primary human T-cells. Human pan-T-cells were isolated from a fresh buffy coat and expanded using CD3/CD28 beads as described previously. One hour after tumor implantation, 10 of the T-cell-implanted mice received 1 mg/kg 1C1m-tB in 100 μl PBS into the tail vein. Control groups (n=10) received 100 μl PBS. The i.v. dosing of 1C1m-tB or PBS vehicle control was repeated 24 h and 48 h after tumor implantation. Subsequently, mice were monitored three times a week and tumors were measured using calipers for a total of 45 days, or until the tumor volume approached ~1000 mm³. NSG mice were bred and housed in a specific and opportunistic pathogen-free environment. All experiments were performed in accordance with the guidelines of the Swiss Federal Veterinary Office and approved by the Cantonal Veterinary Office under the license number 2797.1

Results

The A673 cells rapidly formed tumors in the untreated animals. The co-administration of human T-cells together with the tumor cells substantially delayed tumor outgrowth, but all animals eventually developed tumors. In contrast, following the IV administration of 1C1m-tB, tumor establishment was prevented, or significantly suppressed suggesting an effective delivery of the tB to the tumor site. (FIG. 12). Five out of ten animals treated with 1C1m-tB never developed any tumor, indicating that all tumor cells were eradicated efficiently. Other animals treated with 1C1m-tB developed only flat, scar-like lesions, which never grew to a three-dimensional tumor mass. These results show that an anti-TEM1 TriloBiTE can effectively redirect human T-cells to kill TEM1-expressing target cells in vivo. Further, the administration of 1C1m-tB had no impact on body weight and no apparent toxicities were observed over the course of the experiment. Finally, pharmacokinetic analyses conducted for anti-TEM1 TriloBiTE suggests complete clearance of the molecule in ~48 h.

Example 10: Generation of TEM1-Binding CAR

Instead of using soluble mediators to recruit T-cells to the tumor site, T-cells can also be engineered to express synthetic tumor targeting receptors, termed chimeric antigen receptors (CARs). Anti-TEM1 scFv domains were embedded in a modular second-generation CAR construct comprising a CD28 spacer, transmembrane (TM) domain and cytosolic domain fused to CD3ζ immunoreceptor tyrosine-based activation motif (ITAM) signaling elements (which mediate T-cell activation upon antigen recognition) and an in-frame monomeric GFP (as a reporter) (FIG. 1D).

Generation of CAR-T-Cells

For the manufacturing of CAR-T-cells, sequences encoding anti-TEM1 scFv or anti-CD19 (FMC63; sequence extracted from U.S. Pat. No. 7,446,179) were fused to a spacer/hinge transmembrane region and intracellular costimulatory domain derived from hCD28, followed by an intracellular hCD3ζ signaling domain. The resulting $2^{nd}$ generation CAR cassettes were cloned in-frame to a monomeric green fluorescent protein ORF (TagGFP2, Evrogen) into a modified pRRL lentiviral vector (originally developed by Didier Trono, EPFL). Lentivirus was produced by transient transfection of HEK293T cells using pCMVR8.74 and pMD2.G plasmids for packaging (origin: Didier Trono lab, EPFL) and Turbofect transfection reagent (Life Technologies, #R0532). Virus-containing supernatant was harvested after 48 h, concentrated by ultracentrifugation and 100 µl were added directly to $5\times10^6$ Jurkat-NFAT reporter cells or primary human T-cells pre-plated in 48-well plates on the previous day. Primary T-cells were transduced the day after isolation. All transduced cells were expanded for 10-14 days before performing functional assays.

Jurkat NFAT Activation Reporter Cell Assays

For the assessment of CAR-induced ITAM-signaling, Jurkat-NFAT-mCherry reporter cells were transduced with CAR-GFP constructs as described above. 10-14 days after transduction, $10^6$ transduced Jurkat reporters were seeded in 24-well plates together with $10^6$ target cells. After 24 h of co-culture, Jurkat-NFAT-mCherry cells were harvested by pipetting, washed in FACS buffer (5% FBS, PBS) and analyzed for GFP and mCherry expression by flow cytometry.

Early T-Cell Activation Assay

For measuring early T-cell activation, $0.5\times10^6$ A673 (hTEM1') or AsPC-1 (hTEM1$^-$) target cells were seeded into 24-well plates. Subsequently, $0.5\times10^6$ purified and expanded primary human CAR-T-cells expressing anti-TEM1 or anti-CD19 scFv targeting moieties were added the wells. After 16-18 h of co-culture, the stimulated CAR-T-cells were recovered and washed once in FACS buffer. Cells were blocked with FACS buffer (5% FBS, PBS) for 20 min on ice and incubated with the following staining mix: APC anti-hCD8 (Biolegend #344722), BV785 anti-hCD4 (Biolegend #317441), Alexa Fluor 700 anti-hCD69 (Biolegend #310922), PE anti-hCD25 (Biolegend #302606). After 30 min of incubation on ice, the cells were washed again three times. Immediately before data acquisition, dead cells were stained with 4',6-Diamidino-2-phenylindole (DAPI, 1:2000 dilution). Data was acquired using an LSR-II flow cytometer equipped with FACSDIVA software (BD Biosciences). Data analysis and plotting were carried out using FlowJo v10 (FlowJo LLC).

Real-Time Kinetics of Cell Killing

For the assessment of specific target cell killing using real-time kinetic cell imaging, $2\times10^4$ adherent target cells were seeded in 96-well flat-bottom plates and allowed to attach for ~20 h. When approximately 30% confluency was observed, $1.25\times10^6$ purified and expanded anti-TEM1-CAR-T-cells were added to the plate to reach an E:T ratio of around 5:1. Cytotox Red reagent (Essen Bioscience, #4632) was added to a final dilution of 1:4000, and resultant cell death was monitored as an increase in fluorescence over time, acquiring images every 2 hours. Image acquisition and data analysis were performed on an Incucyte® Live Cell Analysis system (Essen Bioscience).

Results

Figure 13:
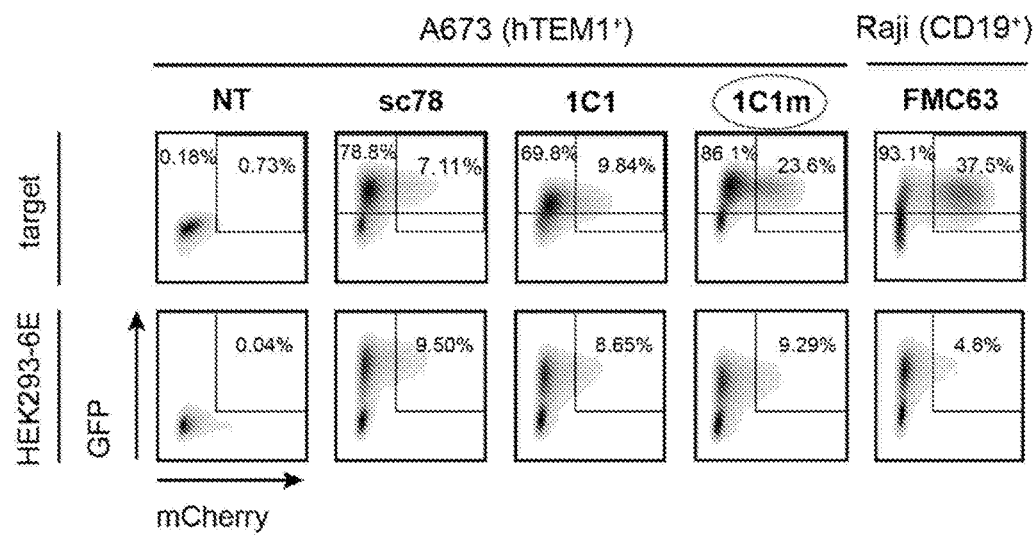
FIG. 13 illustrates Jurkat NFAT-mCherry reporter cells transduced with anti-TEM1 CARs (1C1, 1C1m, sc78) and an anti-CD19 positive control CAR (FMC63), and co-cultured with target cells. All CAR constructs incorporated an in-frame C-terminal green fluorescent protein (GFP) reporter. A673 cells (TEM1+, CD19−) were the co-cultured cognate target cells for the anti-TEM1 CARs, and Raji cells (TEM1−, CD19+) were co-cultured as the cognate target for the anti-CD19 (FMC63) CAR. HEK293-6E (TEM1−, CD19−) cells were co-cultured as a negative control for all CARs. NT, non-transduced.

Anti-TEM1 CAR constructs were generated comprising anti-TEM1 scFv domains derived from antibodies 1C1, 1C1m, and sc78. An anti-CD19 CAR construct (scFv derived from clone FMC63) was used as a control. To demonstrate the activating potential of anti-TEM1 CARs, Jurkat NFAT-reporter cells were engineered to express the fluorescent protein mCherry under the control of an NFAT-driven promoter. The cells were virally transduced with a construct for the expression of the anti-TEM1 CAR. CAR T-cells comprising the high-affinity scFv 1C1m triggered a differential induction of CD3ζ-driven NFAT signaling in response to TEM1-expressing target cells, compared to TEM1$^-$ control cells (FIG. 13).

Figure 14:
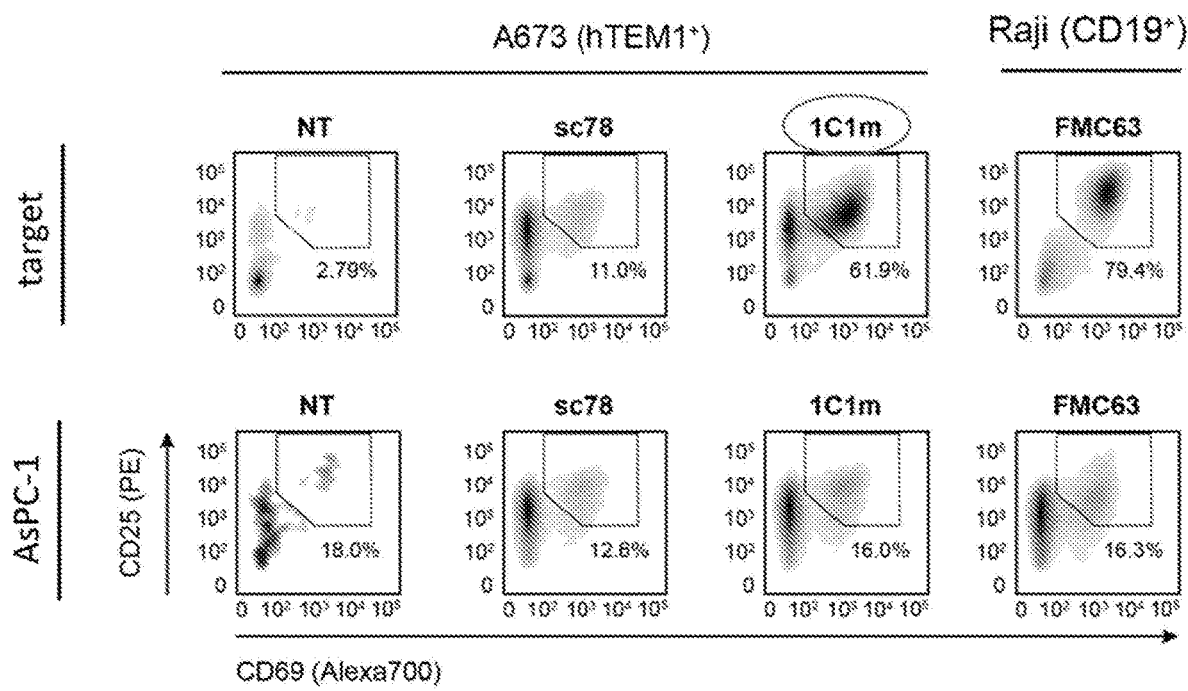
FIG. 14 illustrates that primary human T cells transduced with anti-TEM1 CARs expressed the early activation markers CD69 and CD25 when co-cultured in the presence of A673 target cells (TEM1+, CD19−; upper panel). Negative control data was generated using AsPC-1 cells (TEM1−, CD19−; lower panel). Raji cells (TEM1−, CD19+) were used to stimulate the positive control anti-CD19 (FMC63) CAR T-cells (upper panel, plot on the far right). CD69/CD25 expression was quantified by flow cytometry after 16 h of co-culture. NT, non-transduced.

Further, 1C1m-CAR-T-cells upregulated the T-cell activation markers CD69 and CD25 upon stimulation with TEM1+A673 cells, with the magnitude of expression by 1C1m-CAR-T-cells reaching levels comparable with FMC63-CAR-T-cells co-cultured with CD19' Raji cells. Importantly, CD69/CD25 expression observed in the presence of TEM1$^-$ control cells remained low. Of note, sc78 did not seem to induce significant activation of CD3ζ-ITAM signaling in CAR format (FIG. 14).

Figure 15:
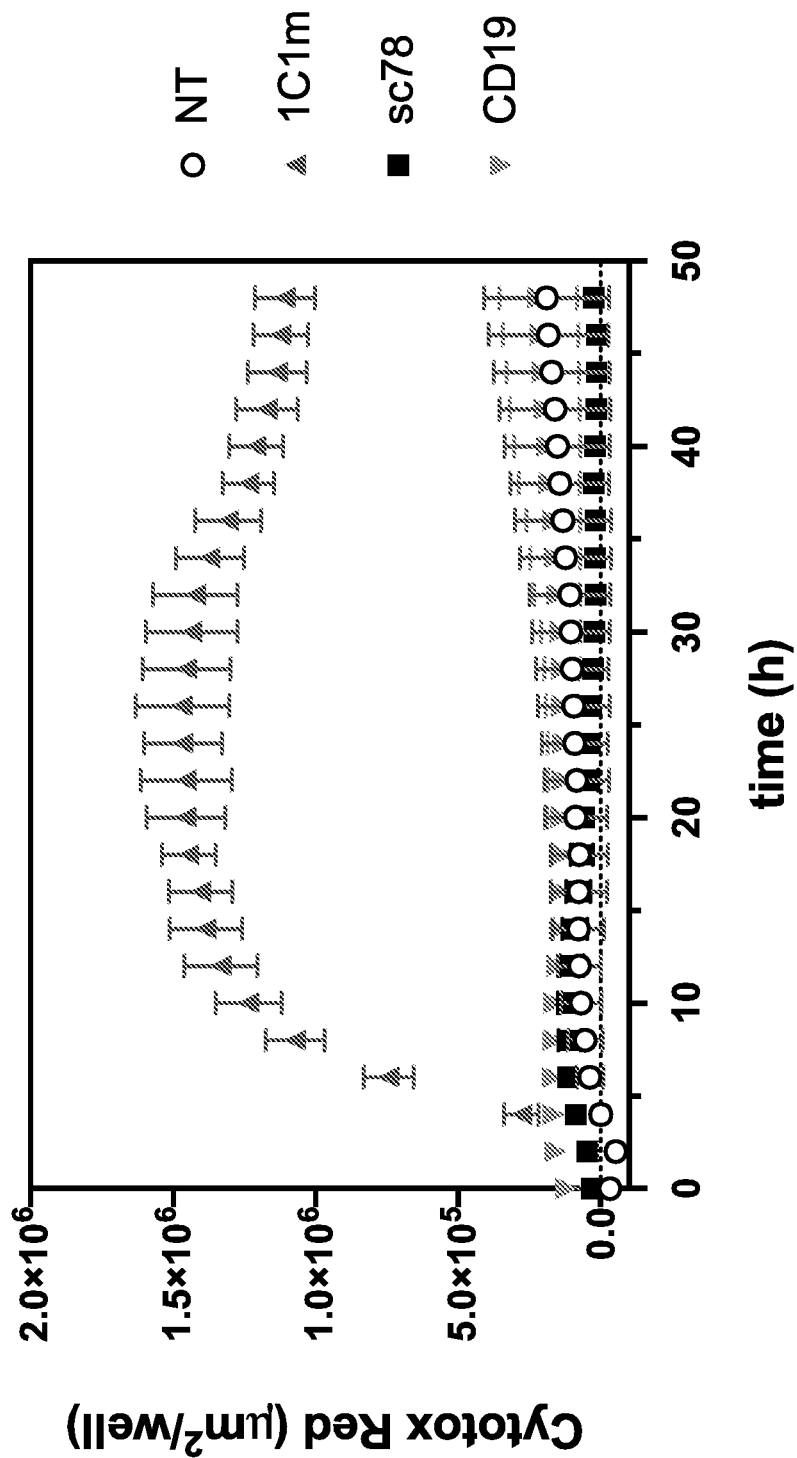
FIG. 15 illustrates real-time kinetics of target cell killing (A673 cells; TEM1+, CD19−) by 1C1m anti-TEM1 CAR-T-cells over the course of 48 h. Cell killing was quantified based on the image-based acquisition of Cytotox Red signal. NT, non-transduced; CD19, an anti-CD19 negative control CAR.

Finally, consistent with the observed up-regulation of CD69/CD25, 1C1m-CAR-T-cells specifically lysed TEM1-expressing A673 tumor cells, in a real-time cytotoxicity assay, while sparing TEM1-negative cells. Maximum lysis was completed after 24 h of co-culture. CAR-T-cells equipped with the previously described clone sc78 did not lyse TEM1$^+$ target cells (FIG. 15).

We claim:

1. An antibody or antigen-binding portion thereof which binds to tumor endothelial marker 1 (TEM1), wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein:

(a) HCDR1 comprises the amino acid sequence of SEQ ID NO:16;

HCDR2 comprises the amino acid sequence of SEQ ID NO:17;

HCDR3 comprises the amino acid sequence of SEQ ID NO:22;

LCDR1 comprises the amino acid sequence of SEQ ID NO:11;

LCDR2 comprises the amino acid sequence SNN; and

LCDR3 comprises the amino acid sequence of SEQ ID NO:13; or (b) HCDR1 comprises the amino acid sequence of SEQ ID NO:16;
HCDR2 comprises the amino acid sequence of SEQ ID NO:17;
HCDR3 comprises the amino acid sequence of SEQ ID NO:18;
LCDR1 comprises the amino acid sequence of SEQ ID NO:11;
LCDR2 comprises the amino acid sequence SNN; and
LCDR3 comprises the amino acid sequence of SEQ ID NO:13.

2. The antibody or antigen-binding portion thereof of claim 1, wherein:
  i. the heavy chain variable region comprises a sequence that is at least 90% identical to SEQ ID NO: 6 and the light chain variable region comprises a sequence that is at least 90% identical to SEQ ID NO: 5; or
  ii. the heavy chain variable region comprises a sequence that is at least 90% identical to SEQ ID NO: 4 and the light chain variable region comprises a sequence that is at least 90% identical to SEQ ID NO: 3.

3. The antibody or antigen-binding portion thereof of claim 1, wherein:
  i. the heavy chain variable region comprises the sequence of SEQ ID NO: 6 and the light chain variable region comprises the sequence of SEQ ID NO: 5; or
  ii. the heavy chain variable region comprises the sequence of SEQ ID NO: 4 and the light chain variable region comprises the sequence of SEQ ID NO: 3.

4. The antigen-binding portion of claim 1, wherein the antigen-binding portion is provided as an IgG, scFv, Fv, Fab', Fab, F(ab')$_2$, scFv-Fc fusion, bidirectional T cell engager, tri-lobed bidirectional T-cell engager, chimeric antigen receptor, or diabody.

5. The antigen-binding portion of claim 1, wherein the antigen-binding portion is a scFv.

6. The antigen-binding portion of claim 5, wherein the antigen-binding portion is fused to the constant region of a Fab.

7. The antigen-binding portion of claim 6, wherein the antigen-binding portion is fused to the constant region of a Fab using a linker comprising SEQ ID NO:46 or SEQ ID NO:47.

8. The antigen-binding portion of claim 5, wherein the Fab comprises a VH-CH1 region or fragment thereof and a VL-CL1 region or fragment thereof, wherein the CH1 region is derived from IgG1, and wherein the CL region is derived from a kappa light chain.

9. The antigen-binding portion of claim 8, wherein:
  (a) the CH1 region is derived from human IgG1 and further comprises a S64E and/or a S66V mutation; and
  (b) the CL region is derived from a human kappa light chain and further comprises a S69L and/or a T71S mutation.

10. The antigen-binding portion of claim 6, wherein the Fab binds to a T-cell antigen.

11. A chimeric antigen receptor (CAR) comprising the scFv of claim 5, the CAR further comprising a transmembrane domain and one or more intracellular domains.

12. The CAR of claim 11, wherein the CAR comprises: a spacer derived from CD28, a transmembrane domain derived from CD28, an intracellular domain derived from CD28, and a domain comprising immunoreceptor tyrosine-based activation motifs (ITAMs) derived from CD3-zeta.

13. The antibody or antigen-binding portion thereof of claim 1, wherein the antibody or antigen-binding portion thereof is a multispecific or a bispecific antibody or antigen-binding portion thereof.

14. The antibody or antigen-binding portion thereof of claim 4, wherein the antibody or antigen-binding portion thereof has isotype IgG1.

15. The antibody or antigen-binding portion thereof of claim 1, wherein the antibody or antigen-binding portion is conjugated to a therapeutic moiety, an imaging moiety, an affinity tag, or a combination thereof.

16. A nucleic acid molecule encoding the antibody or antigen-binding portion thereof of claim 1.

17. A vector comprising the nucleic acid molecule of claim 16.

18. An isolated cell comprising the vector of claim 17.

19. A method of treating cancer in a subject in need thereof, the method comprising administering to the subject an effective amount of the antibody or antigen-binding portion of claim 1.

20. The method of claim 19, wherein the cancer is sarcoma, carcinoma, melanoma, pancreatic cancer, thyroid cancer, lung cancer, colorectal cancer, squamous cancer, prostate cancer, breast cancer, bladder cancer, or gastric cancer.

21. A method of reducing tumor growth in a subject in need thereof, the method comprising administering to the subject an effective amount of the antibody or antigen-binding portion of claim 1.

22. A method of reducing tumor-associated fibrosis in a subject in need thereof, the method comprising administering to the subject an effective amount of the antibody or antigen-binding portion of claim 1.

23. An antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein:
  HCDR1 comprises the amino acid sequence of SEQ ID NO:28;
  HCDR2 comprises the amino acid sequence of SEQ ID NO:29;
  HCDR3 comprises the amino acid sequence of SEQ ID NO:30;
  LCDR1 comprises the amino acid sequence of SEQ ID NO:23;
  LCDR2 comprises the amino acid sequence DAS; and
  LCDR3 comprises the amino acid sequence of SEQ ID NO:25.

24. An antibody or antigen-binding portion thereof which binds to TEM1, wherein the antibody or antigen-binding portion thereof comprises a heavy chain variable region comprising three heavy chain CDRs (HCDR1, HCDR2 and HCDR3) and a light chain variable region comprising three light chain CDRs (LCDR1, LCDR2 and LCDR3), and wherein:
  HCDR1 comprises the amino acid sequence of SEQ ID NO:39;
  HCDR2 comprises the amino acid sequence of SEQ ID NO:40;
  HCDR3 comprises the amino acid sequence of SEQ ID NO:41;
  LCDR1 comprises the amino acid sequence of SEQ ID NO:34;
  LCDR2 comprises the amino acid sequence STY; and LCDR3 comprises the amino acid sequence of SEQ ID NO:36.

25. The antibody or antigen-binding portion thereof of claim 23, wherein the heavy chain variable region comprises a sequence that is at least 90% identical to SEQ ID NO: 8 and the light chain variable region comprises a sequence that is at least 90% identical to SEQ ID NO: 7.

26. The antibody or antigen-binding portion thereof of claim 25, wherein the heavy chain variable region comprises the sequence of SEQ ID NO: 8 and the light chain variable region comprises the sequence of SEQ ID NO: 7.

27. The antibody or antigen-binding portion thereof of claim 24, wherein the heavy chain variable region comprises a sequence that is at least 90% identical to SEQ ID NO: 10 and the light chain variable region comprises a sequence that is at least 90% identical to SEQ ID NO: 9.

28. The antibody or antigen-binding portion thereof of claim 27, wherein the heavy chain variable region comprises the sequence of SEQ ID NO: 10 and the light chain variable region comprises the sequence of SEQ ID NO: 9.

29. A nucleic acid molecule encoding the antibody or antigen-binding portion thereof of claim 23.

30. A nucleic acid molecule encoding the antibody or antigen-binding portion thereof of claim 24.

31. A method of treating cancer in a subject in need thereof, the method comprising administering to the subject an effective amount of the antibody or antigen-binding portion of claim 23.

32. A method of treating cancer in a subject in need thereof, the method comprising administering to the subject an effective amount of the antibody or antigen-binding portion of claim 24.

* * * * *

SEQUENCE LISTING

```
<160> NUMBER OF SEQ ID NOS: 49

<210> SEQ ID NO 1
<211> LENGTH: 757
<212> TYPE: PRT
<213> ORGANISM: Homo sapiens

<400> SEQUENCE: 1

Met Leu Leu Arg Leu Leu Leu Ala Trp Ala Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Arg Thr Phe Leu Glu Ala Trp
```

```
            35                  40                  45
Arg Ala Cys Arg Glu Leu Gly Gly Asp Leu Ala Thr Pro Arg Thr Pro
 50                  55                  60

Glu Glu Ala Gln Arg Val Asp Ser Leu Val Gly Ala Gly Pro Ala Ser
 65                  70                  75                  80

Arg Leu Leu Trp Ile Gly Leu Gln Arg Gln Ala Arg Gln Cys Gln Leu
                     85                  90                  95

Gln Arg Pro Leu Arg Gly Phe Thr Trp Thr Thr Gly Asp Gln Asp Thr
                100                 105                 110

Ala Phe Thr Asn Trp Ala Gln Pro Ala Ser Gly Gly Pro Cys Pro Ala
                115                 120                 125

Gln Arg Cys Val Ala Leu Glu Ala Ser Gly Glu His Arg Trp Leu Glu
            130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
                180                 185                 190

Leu Pro Phe Gly Ser Val Ala Ala Val Gln Cys Gln Ala Gly Arg Gly
            195                 200                 205

Ala Ser Leu Leu Cys Val Lys Gln Pro Glu Gly Gly Val Gly Trp Ser
210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Val Asp Gly His Val Ser Cys
                245                 250                 255

Arg Cys Thr Glu Gly Phe Arg Leu Ala Ala Asp Gly Arg Ser Cys Glu
                260                 265                 270

Asp Pro Cys Ala Gln Ala Pro Cys Glu Gln Cys Glu Pro Gly Gly
                275                 280                 285

Pro Gln Gly Tyr Ser Cys His Cys Arg Leu Gly Phe Arg Pro Ala Glu
            290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
            355                 360                 365

Leu Asp Asp Gly Glu Asp Glu Asp Glu Asp Glu Ala Trp Lys Ala
            370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro
                420                 425                 430

Leu Ser Ala Pro Arg Val Pro Tyr His Ser Ser Val Leu Ser Val Thr
            435                 440                 445

Arg Pro Val Val Val Ser Ala Thr His Pro Thr Leu Pro Ser Ala His
450                 455                 460
```

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
            485                 490                 495

Gln Pro Gly Ile Leu Ser Val Ser His Ser Ala Gln Pro Pro Ala His
        500                 505                 510

Gln Pro Pro Met Ile Ser Thr Lys Tyr Pro Glu Leu Phe Pro Ala His
    515                 520                 525

Gln Ser Pro Met Phe Pro Asp Thr Arg Val Ala Gly Thr Gln Thr Thr
530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
        595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
            660                 665                 670

Glu Ala Gly Leu Ala Glu His Ser Gln Arg Asp Asp Arg Trp Leu Leu
        675                 680                 685

Val Ala Leu Leu Val Pro Thr Cys Val Phe Leu Val Val Leu Leu Ala
    690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
            740                 745                 750

Cys Arg Thr Ser Val
            755

<210> SEQ ID NO 2
<211> LENGTH: 765
<212> TYPE: PRT
<213> ORGANISM: Mus musculus

<400> SEQUENCE: 2

Met Leu Leu Arg Leu Leu Leu Ala Trp Val Ala Ala Val Pro Ala Leu
1               5                   10                  15

Gly Gln Val Pro Trp Thr Pro Glu Pro Arg Ala Ala Cys Gly Pro Ser
            20                  25                  30

Ser Cys Tyr Ala Leu Phe Pro Arg Arg Thr Phe Leu Glu Ala Trp
        35                  40                  45

Arg Ala Cys Arg Glu Leu Gly Gly Asn Leu Ala Thr Pro Arg Thr Pro
    50                  55                  60

Glu Glu Ala Gln Arg Val Asp Ser Leu Val Gly Val Gly Pro Ala Asn

-continued

```
             65                  70                  75                  80
Gly Leu Leu Trp Ile Gly Leu Gln Arg Gln Ala Arg Gln Cys Gln Pro
                     85                  90                  95

Gln Arg Pro Leu Arg Gly Phe Ile Trp Thr Thr Gly Asp Gln Asp Thr
                100                 105                 110

Ala Phe Thr Asn Trp Ala Gln Pro Ala Thr Glu Gly Pro Cys Pro Ala
            115                 120                 125

Gln Arg Cys Ala Ala Leu Glu Ala Ser Gly Glu His Arg Trp Leu Glu
        130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Pro Leu Glu Val Gly Gln Ala Gly Pro
                165                 170                 175

Ala Val Tyr Thr Thr Pro Phe Asn Leu Val Ser Ser Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Ser Gly Gly Val Gly Trp Ser
210                 215                 220

Gln Thr Gly Pro Leu Cys Pro Gly Thr Gly Cys Gly Pro Asp Asn Gly
225                 230                 235                 240

Gly Cys Glu His Glu Cys Val Glu Val Asp Gly Ala Val Ser Cys
                245                 250                 255

Arg Cys Ser Glu Gly Phe Arg Leu Ala Ala Asp Gly His Ser Cys Glu
            260                 265                 270

Asp Pro Cys Ala Gln Ala Pro Cys Glu Gln Cys Glu Pro Gly Gly
        275                 280                 285

Pro Gln Gly Tyr Ser Cys His Cys Arg Leu Gly Phe Arg Pro Ala Glu
            290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
            340                 345                 350

Ala Gly Ala Met Gly Ala Gln Ala Ser Gln Asp Leu Arg Asp Glu Leu
        355                 360                 365

Leu Asp Asp Gly Glu Glu Gly Glu Asp Glu Glu Pro Trp Glu Asp
370                 375                 380

Phe Asp Gly Thr Trp Thr Glu Glu Gln Gly Ile Leu Trp Leu Ala Pro
385                 390                 395                 400

Thr His Pro Pro Asp Phe Gly Leu Pro Tyr Arg Pro Asn Phe Pro Gln
                405                 410                 415

Asp Gly Glu Pro Gln Arg Leu His Leu Glu Pro Thr Trp Pro Pro
            420                 425                 430

Leu Ser Ala Pro Arg Gly Pro Tyr His Ser Val Ser Ala Thr
        435                 440                 445

Arg Pro Met Val Ile Ser Ala Thr Arg Pro Thr Leu Pro Ser Ala His
            450                 455                 460

Lys Thr Ser Val Ile Ser Ala Thr Arg Pro Leu Ser Pro Val His
465                 470                 475                 480

Pro Pro Ala Met Ala Pro Ala Thr Pro Ala Val Phe Ser Glu His
                485                 490                 495
```

```
Gln Ile Pro Lys Ile Lys Ala Asn Tyr Pro Asp Leu Pro Phe Gly His
            500                 505                 510
Lys Pro Gly Ile Thr Ser Ala Thr His Pro Ala Arg Ser Pro Pro Tyr
            515                 520                 525
Gln Pro Pro Ile Ile Ser Thr Asn Tyr Pro Gln Val Phe Pro Pro His
            530                 535                 540
Gln Ala Pro Met Ser Pro Asp Thr His Thr Ile Thr Tyr Leu Pro Pro
545                 550                 555                 560
Val Pro Pro His Leu Asp Pro Gly Asp Thr Thr Ser Lys Ala His Gln
            565                 570                 575
His Pro Leu Leu Pro Asp Ala Pro Gly Ile Arg Thr Gln Ala Pro Gln
            580                 585                 590
Leu Ser Val Ser Ala Leu Gln Pro Pro Leu Pro Thr Asn Ser Arg Ser
            595                 600                 605
Ser Val His Glu Thr Pro Val Pro Ala Ala Asn Gln Pro Pro Ala Phe
            610                 615                 620
Pro Ser Ser Pro Leu Pro Pro Gln Arg Pro Thr Asn Gln Thr Ser Ser
625                 630                 635                 640
Ile Ser Pro Thr His Ser Tyr Ser Arg Ala Pro Leu Val Pro Arg Glu
            645                 650                 655
Gly Val Pro Ser Pro Lys Ser Val Pro Gln Leu Pro Ser Val Pro Ser
            660                 665                 670
Thr Ala Ala Pro Thr Ala Leu Ala Glu Ser Gly Leu Ala Gly Gln Ser
            675                 680                 685
Gln Arg Asp Asp Arg Trp Leu Leu Val Ala Leu Leu Val Pro Thr Cys
            690                 695                 700
Val Phe Leu Val Val Leu Leu Ala Leu Gly Ile Val Tyr Cys Thr Arg
705                 710                 715                 720
Cys Gly Ser His Ala Pro Asn Lys Arg Ile Thr Asp Cys Tyr Arg Trp
            725                 730                 735
Val Thr His Ala Gly Asn Lys Ser Ser Thr Glu Pro Met Pro Pro Arg
            740                 745                 750
Gly Ser Leu Thr Gly Val Gln Thr Cys Arg Thr Ser Val
            755                 760                 765

<210> SEQ ID NO 3
<211> LENGTH: 110
<212> TYPE: PRT
<213> ORGANISM: Homo sapiens

<400> SEQUENCE: 3

Gln Pro Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
            35                  40                  45
Ile Tyr Ser Asn Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Ala Leu Val Phe Gly Gly Gly Thr Lys Leu Thr Val Leu
```

<210> SEQ ID NO 4
<211> LENGTH: 122
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Leu Thr Ser Tyr Tyr Gly Asp Pro Thr Gly Phe Asp Tyr Trp
                100                 105                 110

Gly Gln Gly Thr Leu Val Thr Val Ser Ser
        115                 120

<210> SEQ ID NO 5
<211> LENGTH: 110
<212> TYPE: PRT
<213> ORGANISM: Homo sapiens

<400> SEQUENCE: 5

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Leu Val Phe Gly Gly Gly Thr Lys Leu Thr Val Leu
                100                 105                 110

<210> SEQ ID NO 6
<211> LENGTH: 122
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

```
Gly Gly Ile Ile Pro Ile Phe Gly Thr Ala Asn Tyr Ala Gln Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Ser Leu Ile Ser Tyr Tyr Gly Asp Pro Thr Gly Phe Asp Tyr Trp
                100                 105                 110
Gly Gln Gly Thr Leu Val Thr Val Ser Ser
                115                 120

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Pro Thr Leu Ser Ala Ser Val Gly
 1               5                  10                  15
Asp Arg Val Thr Ile Thr Cys Arg Ala Ser Gln Ser Ile Ser Arg Trp
                 20                  25                  30
Leu Ala Trp Tyr Gln Gln Lys Pro Gly Lys Ala Pro Asn Leu Leu Ile
                 35                  40                  45
Tyr Asp Ala Ser Asn Leu Gln Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Asp Asp Phe Gly Thr Tyr Tyr Cys Gln Gln Tyr Lys Asn Tyr Ser Pro
                 85                  90                  95
Thr Phe Gly Gln Gly Thr Lys Leu Glu Ile Lys
                100                 105

<210> SEQ ID NO 8
<211> LENGTH: 121
<212> TYPE: PRT
<213> ORGANISM: Homo sapiens

<400> SEQUENCE: 8

Glu Val Gln Leu Val Glu Thr Gly Gly Gly Leu Val Lys Pro Gly Gly
 1               5                  10                  15
Ser Leu Arg Leu Ser Cys Ala Ala Ser Gly Phe Thr Phe Asn Thr Tyr
                 20                  25                  30
Thr Met Asn Trp Val Arg Gln Ala Pro Gly Lys Gly Leu Glu Trp Val
                 35                  40                  45
Ser Ser Ile Ser Ser Ser Ser Thr Tyr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Lys Ser Ile Val Gly Ala Thr His Asp Ala Phe Asp Ile Trp Gly
                100                 105                 110
Gln Gly Thr Met Val Thr Val Ser Ser
                115                 120

<210> SEQ ID NO 9
```

```
<211> LENGTH: 110
<212> TYPE: PRT
<213> ORGANISM: Homo sapiens

<400> SEQUENCE: 9

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Thr Val Asn Trp Tyr Gln Leu Pro Gly Thr Ala Pro Lys Leu Leu
            35                  40                  45

Ile Tyr Ser Thr Tyr Gln Arg Pro Ser Val Pro Gly Arg Phe Ser
50                  55                  60

Gly Ser Lys Ser Ala Thr Ser Ala Ser Leu Ala Ile Ser Gly Leu Gln
65              70                  75                  80

Ser Glu Asp Glu Ala Asp Tyr Tyr Cys Ala Thr Trp Asp Asp Ser Leu
                85                  90                  95

Asn Gly Val Val Phe Gly Gly Gly Thr Lys Leu Thr Val Leu
            100                 105                 110

<210> SEQ ID NO 10
<211> LENGTH: 119
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Val Arg Gly Ser His Pro Trp Phe Asp Pro Trp Gly Gln Gly
            100                 105                 110

Thr Leu Val Thr Val Ser Ser
        115

<210> SEQ ID NO 11
<211> LENGTH: 8
<212> TYPE: PRT
<213> ORGANISM: Homo sapiens

<400> SEQUENCE: 11

Ser Ser Asn Ile Gly Ser Asn Thr
1               5

<210> SEQ ID NO 12
<211> LENGTH: 8
<212> TYPE: PRT
<213> ORGANISM: Homo sapiens

<400> SEQUENCE: 12

Ser Ser Asn Ile Gly Ser Asn Thr
```

```
<210> SEQ ID NO 13
<211> LENGTH: 11
<212> TYPE: PRT
<213> ORGANISM: Homo sapiens

<400> SEQUENCE: 13

Ala Ala Trp Asp Asp Ser Leu Asn Ala Leu Val
1               5                   10

<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Ser Asn Thr Val Asn
1               5                   10

<210> SEQ ID NO 15
<211> LENGTH: 7
<212> TYPE: PRT
<213> ORGANISM: Homo sapiens

<400> SEQUENCE: 15

Ser Asn Asn Gln Arg Pro Ser
1               5

<210> SEQ ID NO 16
<211> LENGTH: 8
<212> TYPE: PRT
<213> ORGANISM: Homo sapiens

<400> SEQUENCE: 16

Gly Gly Thr Phe Ser Ser Tyr Ala
1               5

<210> SEQ ID NO 17
<211> LENGTH: 8
<212> TYPE: PRT
<213> ORGANISM: Homo sapiens

<400> SEQUENCE: 17

Ile Ile Pro Ile Phe Gly Thr Ala
1               5

<210> SEQ ID NO 18
<211> LENGTH: 15
<212> TYPE: PRT
<213> ORGANISM: Homo sapiens

<400> SEQUENCE: 18

Ala Ser Leu Thr Ser Tyr Tyr Gly Asp Pro Thr Gly Phe Asp Tyr
1               5                   10                  15

<210> SEQ ID NO 19
<211> LENGTH: 5
<212> TYPE: PRT
<213> ORGANISM: Homo sapiens

<400> SEQUENCE: 19

Ser Tyr Ala Ile Ser
1               5
```

<210> SEQ ID NO 20
<211> LENGTH: 17
<212> TYPE: PRT
<213> ORGANISM: Homo sapiens

<400> SEQUENCE: 20

Gly Ile Ile Pro Ile Phe Gly Thr Ala Asn Tyr Ala Gln Lys Phe Gln
1               5                   10                  15

Gly

<210> SEQ ID NO 21
<211> LENGTH: 13
<212> TYPE: PRT
<213> ORGANISM: Homo sapiens

<400> SEQUENCE: 21

Leu Thr Ser Tyr Tyr Gly Asp Pro Thr Gly Phe Asp Tyr
1               5                   10

<210> SEQ ID NO 22
<211> LENGTH: 15
<212> TYPE: PRT
<213> ORGANISM: Homo sapiens

<400> SEQUENCE: 22

Ala Ser Leu Ile Ser Tyr Tyr Gly Asp Pro Thr Gly Phe Asp Tyr
1               5                   10                  15

<210> SEQ ID NO 23
<211> LENGTH: 6
<212> TYPE: PRT
<213> ORGANISM: Homo sapiens

<400> SEQUENCE: 23

Gln Ser Ile Ser Arg Trp
1               5

<210> SEQ ID NO 24
<211> LENGTH: 6
<212> TYPE: PRT
<213> ORGANISM: Homo sapiens

<400> SEQUENCE: 24

Gln Ser Ile Ser Arg Trp
1               5

<210> SEQ ID NO 25
<211> LENGTH: 9
<212> TYPE: PRT
<213> ORGANISM: Homo sapiens

<400> SEQUENCE: 25

Gln Gln Tyr Lys Asn Tyr Ser Pro Thr
1               5

<210> SEQ ID NO 26
<211> LENGTH: 11
<212> TYPE: PRT
<213> ORGANISM: Homo sapiens

<400> SEQUENCE: 26

Arg Ala Ser Gln Ser Ile Ser Arg Trp Leu Ala
1               5                   10

```
<210> SEQ ID NO 27
<211> LENGTH: 7
<212> TYPE: PRT
<213> ORGANISM: Homo sapiens

<400> SEQUENCE: 27

Asp Ala Ser Asn Leu Gln Ser
1               5

<210> SEQ ID NO 28
<211> LENGTH: 8
<212> TYPE: PRT
<213> ORGANISM: Homo sapiens

<400> SEQUENCE: 28

Gly Phe Thr Phe Asn Thr Tyr Thr
1               5

<210> SEQ ID NO 29
<211> LENGTH: 8
<212> TYPE: PRT
<213> ORGANISM: Homo sapiens

<400> SEQUENCE: 29

Ile Ser Ser Ser Ser Thr Tyr Ile
1               5

<210> SEQ ID NO 30
<211> LENGTH: 14
<212> TYPE: PRT
<213> ORGANISM: Homo sapiens

<400> SEQUENCE: 30

Ala Lys Ser Ile Val Gly Ala Thr His Asp Ala Phe Asp Ile
1               5                   10

<210> SEQ ID NO 31
<211> LENGTH: 5
<212> TYPE: PRT
<213> ORGANISM: Homo sapiens

<400> SEQUENCE: 31

Thr Tyr Thr Met Asn
1               5

<210> SEQ ID NO 32
<211> LENGTH: 17
<212> TYPE: PRT
<213> ORGANISM: Homo sapiens

<400> SEQUENCE: 32

Ser Ile Ser Ser Ser Ser Thr Tyr Ile Tyr Tyr Ala Asp Ser Val Lys
1               5                   10                  15

Gly

<210> SEQ ID NO 33
<211> LENGTH: 12
<212> TYPE: PRT
<213> ORGANISM: Homo sapiens

<400> SEQUENCE: 33

Ser Ile Val Gly Ala Thr His Asp Ala Phe Asp Ile
1               5                   10
```

<210> SEQ ID NO 34
<211> LENGTH: 8
<212> TYPE: PRT
<213> ORGANISM: Homo sapiens

<400> SEQUENCE: 34

Ser Ser Asn Ile Gly Ile Asn Thr
1               5

<210> SEQ ID NO 35
<211> LENGTH: 8
<212> TYPE: PRT
<213> ORGANISM: Homo sapiens

<400> SEQUENCE: 35

Ser Ser Asn Ile Gly Ile Asn Thr
1               5

<210> SEQ ID NO 36
<211> LENGTH: 11
<212> TYPE: PRT
<213> ORGANISM: Homo sapiens

<400> SEQUENCE: 36

Ala Thr Trp Asp Asp Ser Leu Asn Gly Val Val
1               5                   10

<210> SEQ ID NO 37
<211> LENGTH: 13
<212> TYPE: PRT
<213> ORGANISM: Homo sapiens

<400> SEQUENCE: 37

Ser Gly Ser Ser Ser Asn Ile Gly Ile Asn Thr Val Asn
1               5                   10

<210> SEQ ID NO 38
<211> LENGTH: 7
<212> TYPE: PRT
<213> ORGANISM: Homo sapiens

<400> SEQUENCE: 38

Ser Thr Tyr Gln Arg Pro Ser
1               5

<210> SEQ ID NO 39
<211> LENGTH: 8
<212> TYPE: PRT
<213> ORGANISM: Homo sapiens

<400> SEQUENCE: 39

Gly Tyr Thr Phe Thr Gly Tyr Tyr
1               5

<210> SEQ ID NO 40
<211> LENGTH: 8
<212> TYPE: PRT
<213> ORGANISM: Homo sapiens

<400> SEQUENCE: 40

Ile Asn Pro Asn Ser Gly Gly Thr
1               5

<210> SEQ ID NO 41

```
<210> SEQ ID NO 41
<211> LENGTH: 12
<212> TYPE: PRT
<213> ORGANISM: Homo sapiens

<400> SEQUENCE: 41

Ala Arg Val Arg Gly Ser His Pro Trp Phe Asp Pro
1               5                   10

<210> SEQ ID NO 42
<211> LENGTH: 5
<212> TYPE: PRT
<213> ORGANISM: Homo sapiens

<400> SEQUENCE: 42

Gly Tyr Tyr Met His
1               5

<210> SEQ ID NO 43
<211> LENGTH: 17
<212> TYPE: PRT
<213> ORGANISM: Homo sapiens

<400> SEQUENCE: 43

Trp Ile Asn Pro Asn Ser Gly Gly Thr Asn Tyr Ala Gln Lys Phe Gln
1               5                   10                  15

Gly

<210> SEQ ID NO 44
<211> LENGTH: 122
<212> TYPE: PRT
<213> ORGANISM: Artificial Sequence
<220> FEATURE:
<223> OTHER INFORMATION: synthetic peptide

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
        50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser
            115                 120

<210> SEQ ID NO 45
<211> LENGTH: 107
<212> TYPE: PRT
<213> ORGANISM: Artificial Sequence
<220> FEATURE:
<223> OTHER INFORMATION: synthetic peptide

<400> SEQUENCE: 45

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 46
<211> LENGTH: 13
<212> TYPE: PRT
<213> ORGANISM: Artificial Sequence
<220> FEATURE:
<223> OTHER INFORMATION: synthetic peptide

<400> SEQUENCE: 46

Gly Gly Gly Gly Ser Gly Gly Ser Gly Gly Gly Ser
1               5                   10

<210> SEQ ID NO 47
<211> LENGTH: 15
<212> TYPE: PRT
<213> ORGANISM: Artificial Sequence
<220> FEATURE:
<223> OTHER INFORMATION: synthetic peptide

<400> SEQUENCE: 47

Asp Lys Thr His Thr Gly Gly Gly Ser Gly Gly Gly Ser
1               5                   10                  15

<210> SEQ ID NO 48
<211> LENGTH: 13
<212> TYPE: PRT
<213> ORGANISM: Homo sapiens

<400> SEQUENCE: 48

Leu Ile Ser Tyr Tyr Gly Asp Pro Thr Gly Phe Asp Tyr
1               5                   10

<210> SEQ ID NO 49
<211> LENGTH: 10
<212> TYPE: PRT
<213> ORGANISM: Homo sapiens

<400> SEQUENCE: 49

Val Arg Gly Ser His Pro Trp Phe Asp Pro
1               5                   10
```